(12) United States Patent
Temby et al.

(10) Patent No.: US 11,399,153 B2
(45) Date of Patent: Jul. 26, 2022

(54) PORTABLE TELEPRESENCE APPARATUS

(75) Inventors: Kelton Temby, Goleta, CA (US); Charles S Jordan, Santa Barbara, CA (US); Daniel S Sanchez, Summerland, CA (US); Steven E Butner, Santa Barbara, CA (US); Derek J Walters, Buellton, CA (US); Fuji Lai, Goleta, CA (US); Kevin P Hanrahan, Santa Barbara, CA (US); Joshua A Bouganim, Goleta, CA (US); James Rosenthal, Santa Barbara, CA (US)

(73) Assignee: TELADOC HEALTH, INC., Purchase, NY (US)

( * ) Notice: Subject to any disclaimer, the term of this patent is extended or adjusted under 35 U.S.C. 154(b) by 81 days.

(21) Appl. No.: 12/868,859

(22) Filed: Aug. 26, 2010

(65) Prior Publication Data

US 2011/0213210 A1    Sep. 1, 2011

Related U.S. Application Data

(63) Continuation-in-part of application No. 12/548,122, filed on Aug. 26, 2009, now Pat. No. 8,384,755.

(60) Provisional application No. 61/399,637, filed on Jul. 14, 2010.

(51) Int. Cl.
| | |
|---|---|
| *H04N 7/14* | (2006.01) |
| *H04N 21/4788* | (2011.01) |
| *H04N 21/4227* | (2011.01) |
| *G16H 40/67* | (2018.01) |

(52) U.S. Cl.
CPC ............ *H04N 7/142* (2013.01); *G16H 40/67* (2018.01); *H04N 21/4227* (2013.01); *H04N 21/4788* (2013.01)

(58) Field of Classification Search
USPC .................................. 348/14.01–14.05, 10.08
See application file for complete search history.

(56) References Cited

U.S. PATENT DOCUMENTS

| | | | |
|---|---|---|---|
| 3,821,995 | A | 7/1974 | Aghnides |
| 4,107,689 | A | 8/1978 | Jellinek |
| 4,213,182 | A | 7/1980 | Eichelberger et al. |

(Continued)

FOREIGN PATENT DOCUMENTS

| | | |
|---|---|---|
| AU | 1216200 A | 5/2000 |
| CA | 2289697 | 11/1998 |

(Continued)

OTHER PUBLICATIONS

US 8,248,451 B2, 08/2012, Wang et al. (withdrawn)

(Continued)

*Primary Examiner* — Duc Nguyen
*Assistant Examiner* — Assad Mohammed

(57) ABSTRACT

A telepresence system that includes a portable telepresence apparatus coupled to a remote control station. The telepresence apparatus comprises a monitor, a camera, a speaker, a microphone and a viewfinder screen coupled to a housing. The view finder screen allows the user to view the image being captured by the camera. The portable telepresence apparatus is a hand held device that can be moved by a holder of the device in response to audio commands from the remote station. The telepresence apparatus can be used by medical personnel to remotely view a patient in a fast and efficient manner.

11 Claims, 9 Drawing Sheets

(56) References Cited

U.S. PATENT DOCUMENTS

| | | |
|---|---|---|
| 4,413,693 A | 11/1983 | Derby |
| 4,471,354 A | 8/1984 | Smith |
| 4,519,466 A | 5/1985 | Shiraishi |
| 4,553,309 A | 11/1985 | Hess et al. |
| 4,572,594 A | 2/1986 | Schwartz |
| 4,625,274 A | 11/1986 | Schroeder |
| 4,638,445 A | 1/1987 | Mattaboni |
| 4,652,204 A | 3/1987 | Arnett |
| 4,669,168 A | 6/1987 | Tamura et al. |
| 4,679,152 A | 7/1987 | Perdue |
| 4,697,278 A | 9/1987 | Fleischer |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 11/1988 | George et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Crane et al. |
| 5,006,988 A | 4/1991 | Borenstein et al. |
| 5,040,116 A | 8/1991 | Evans, Jr. et al. |
| 5,051,906 A | 9/1991 | Evans, Jr. et al. |
| 5,073,749 A | 12/1991 | Kanayama |
| 5,084,828 A | 1/1992 | Kaufman |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,220,263 A | 6/1993 | Onishi et al. |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matsen, III et al. |
| 5,262,944 A | 11/1993 | Weisner et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey |
| 5,374,879 A | 12/1994 | Pin |
| 5,375,195 A | 12/1994 | Johnston |
| 5,400,068 A | 3/1995 | Ishida et al. |
| 5,413,693 A | 5/1995 | Redepenning |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David |
| 5,442,728 A | 8/1995 | Kaufman et al. |
| 5,462,051 A | 10/1995 | Oka |
| 5,486,853 A | 1/1996 | Baxter et al. |
| 5,510,832 A | 4/1996 | Garcia |
| 5,511,147 A | 4/1996 | Abdel-Malek |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,617,539 A | 4/1997 | Ludwig et al. |
| 5,619,341 A | 4/1997 | Auyeung et al. |
| 5,623,679 A | 4/1997 | Rivette et al. |
| 5,630,566 A | 5/1997 | Case |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,695 A | 11/1997 | Bauer |
| 5,701,904 A | 12/1997 | Simmons et al. |
| 5,734,805 A | 3/1998 | Isensee et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Colens |
| 5,793,365 A | 8/1998 | Tang et al. |
| 5,801,755 A | 9/1998 | Echerer |
| 5,802,494 A | 9/1998 | Kuno |
| 5,836,872 A | 11/1998 | Kenet |
| 5,838,575 A | 11/1998 | Lion |
| 5,844,599 A | 12/1998 | Hildin |
| 5,857,534 A | 1/1999 | DeVault et al. |
| 5,867,494 A | 2/1999 | Krishnaswamy et al. |
| 5,867,653 A | 2/1999 | Aras et al. |
| 5,871,451 A | 2/1999 | Unger et al. |
| 5,872,922 A | 2/1999 | Hogan et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober et al. |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |
| 6,091,219 A | 7/2000 | Maruo et al. |
| 6,113,343 A | 9/2000 | Goldenberg et al. |
| 6,133,944 A | 10/2000 | Braun |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,189,034 B1 | 2/2001 | Riddle |
| 6,201,984 B1 | 3/2001 | Funda et al. |
| 6,211,903 B1 * | 4/2001 | Bullister .................... 348/14.16 |
| 6,219,587 B1 | 4/2001 | Ahlin et al. |
| 6,232,735 B1 | 5/2001 | Baba |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |

(56) References Cited

U.S. PATENT DOCUMENTS

| | | |
|---|---|---|
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,292,714 B1 | 9/2001 | Okabayashi |
| 6,304,050 B1 | 10/2001 | Skaar et al. |
| 6,314,631 B1 | 11/2001 | Pryor |
| 6,317,652 B1 | 11/2001 | Osada |
| 6,317,953 B1 | 11/2001 | Pryor |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,346,950 B1 | 2/2002 | Jouppi |
| 6,346,962 B1 | 2/2002 | Goodridge |
| 6,369,847 B1 | 4/2002 | James et al. |
| 6,373,855 B1 | 4/2002 | Downing et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Wada |
| 6,411,055 B1 | 6/2002 | Fujita et al. |
| 6,430,471 B1 | 8/2002 | Kintou et al. |
| 6,430,475 B2 | 8/2002 | Okamoto |
| 6,438,457 B1 | 8/2002 | Yokoo |
| 6,445,964 B1 | 9/2002 | White et al. |
| 6,449,762 B1 | 9/2002 | McElvain |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu |
| 6,543,899 B2 | 4/2003 | Covannon et al. |
| 6,549,215 B2 | 4/2003 | Jouppi |
| 6,563,533 B1 | 5/2003 | Colby |
| 6,567,038 B1 | 5/2003 | Granot et al. |
| 6,580,246 B2 | 6/2003 | Jacobs |
| 6,581,798 B2 | 6/2003 | Lift et al. |
| 6,584,376 B1 | 6/2003 | Van Kommer |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 | 7/2003 | Nowlin et al. |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,667,592 B2 | 12/2003 | Jacobs et al. |
| 6,674,259 B1 | 1/2004 | Norman et al. |
| 6,684,129 B2 | 1/2004 | Salisbury et al. |
| 6,691,000 B2 | 2/2004 | Nagai et al. |
| 6,693,585 B1 | 2/2004 | Macleod |
| 6,710,797 B1 | 3/2004 | McNelley et al. |
| 6,724,823 B2 | 4/2004 | Rovati et al. |
| 6,728,599 B2 | 4/2004 | Wang et al. |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi et al. |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,893,267 B1 | 5/2005 | Yueh |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe |
| 6,957,712 B2 | 10/2005 | Song et al. |
| 6,958,706 B2 | 10/2005 | Chaco et al. |
| 6,965,394 B2 | 11/2005 | Gutta et al. |
| 6,990,112 B1 | 1/2006 | Brent et al. |
| 6,995,664 B1 | 2/2006 | Darling et al. |
| 7,007,235 B1 | 2/2006 | Hussein et al. |
| 7,011,538 B2 | 3/2006 | Chang |
| 7,015,934 B2 | 3/2006 | Toyama et al. |
| RE39,080 E | 4/2006 | Johnston |
| 7,030,757 B2 | 4/2006 | Matsuhira et al. |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |

(56) References Cited

U.S. PATENT DOCUMENTS

| | | |
|---|---|---|
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai et al. |
| 7,219,364 B2 | 5/2007 | Bolle et al. |
| 7,222,000 B2 | 5/2007 | Wang et al. |
| 7,227,334 B2 | 6/2007 | Yang et al. |
| 7,256,708 B2 | 8/2007 | Rosenfeld |
| 7,262,573 B2 | 8/2007 | Wang et al. |
| 7,283,153 B2 | 10/2007 | Provost et al. |
| 7,289,883 B2 | 10/2007 | Wang et al. |
| 7,292,257 B2 | 11/2007 | Kang et al. |
| 7,292,912 B2 | 11/2007 | Way et al. |
| 7,305,114 B2 | 12/2007 | Wolff et al. |
| 7,317,685 B1 | 1/2008 | Flott et al. |
| 7,321,807 B2 | 1/2008 | Wang et al. |
| 7,332,890 B2 | 2/2008 | Cohen et al. |
| 7,333,642 B2 | 2/2008 | Green |
| 7,346,429 B2 | 3/2008 | Goldenberg et al. |
| 7,352,153 B2 | 4/2008 | Yan |
| 7,363,121 B1 | 4/2008 | Chen et al. |
| 7,382,399 B1 | 6/2008 | Mccall |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 | 7/2008 | O'Rourke |
| 7,421,470 B2 | 9/2008 | Ludwig et al. |
| 7,430,209 B2 | 9/2008 | Porter |
| 7,432,949 B2 * | 10/2008 | Remy et al. ............... 348/14.02 |
| 7,433,921 B2 | 10/2008 | Ludwig et al. |
| 7,441,953 B2 | 10/2008 | Banks |
| 7,467,211 B1 | 12/2008 | Herman et al. |
| 7,483,867 B2 | 1/2009 | Ansari et al. |
| 7,492,731 B2 | 2/2009 | Hagendorf |
| 7,510,428 B2 | 3/2009 | Obata et al. |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,557,758 B2 | 7/2009 | Rofougaran |
| 7,587,260 B2 | 9/2009 | Bruemmer et al. |
| 7,587,512 B2 | 9/2009 | Ta et al. |
| 7,590,060 B2 | 9/2009 | Miceli |
| 7,593,030 B2 | 9/2009 | Way et al. |
| 7,599,290 B2 | 10/2009 | Dos Remedios et al. |
| 7,624,166 B2 | 11/2009 | Foote et al. |
| 7,630,314 B2 | 12/2009 | Dos Remedios et al. |
| 7,631,833 B1 | 12/2009 | Ghaleb et al. |
| 7,643,051 B2 | 1/2010 | Sandberg et al. |
| 7,647,320 B2 | 1/2010 | Mok et al. |
| 7,657,560 B1 | 2/2010 | Dirienzo |
| 7,680,038 B1 | 3/2010 | Gourlay |
| 7,693,757 B2 | 4/2010 | Zimmerman |
| 7,698,432 B2 | 4/2010 | Short et al. |
| 7,703,113 B2 | 4/2010 | Dawson |
| 7,719,229 B2 | 5/2010 | Kaneko et al. |
| 7,737,993 B2 | 6/2010 | Kaasila et al. |
| 7,739,383 B1 | 6/2010 | Short et al. |
| 7,756,614 B2 | 7/2010 | Jouppi |
| 7,761,185 B2 * | 7/2010 | Wang .................... A61B 34/35 700/259 |
| 7,769,492 B2 | 8/2010 | Wang et al. |
| 7,769,705 B1 | 8/2010 | Luechtefeld |
| 7,774,158 B2 | 8/2010 | Goncalves et al. |
| 7,813,836 B2 | 10/2010 | Wang et al. |
| 7,831,575 B2 | 11/2010 | Trossell et al. |
| 7,835,775 B2 * | 11/2010 | Sawayama et al. ....... 455/575.3 |
| 7,860,680 B2 | 12/2010 | Arms et al. |
| 7,861,366 B2 | 1/2011 | Hahm et al. |
| 7,885,822 B2 | 2/2011 | Akers et al. |
| 7,890,382 B2 | 2/2011 | Robb et al. |
| 7,912,583 B2 | 3/2011 | Gutmann et al. |
| RE42,288 E | 4/2011 | Degioanni |
| 7,924,323 B2 | 4/2011 | Walker et al. |
| 7,949,616 B2 | 5/2011 | Levy et al. |
| 7,956,894 B2 | 6/2011 | Akers et al. |
| 7,957,837 B2 | 6/2011 | Ziegler et al. |
| 7,982,763 B2 | 7/2011 | King |
| 7,982,769 B2 | 7/2011 | Jenkins et al. |
| 7,987,069 B2 | 7/2011 | Rodgers et al. |
| 8,077,963 B2 | 12/2011 | Wang et al. |
| 8,116,910 B2 | 2/2012 | Walters et al. |
| 8,126,960 B2 | 2/2012 | Obradovich et al. |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Yulun et al. |
| 8,212,533 B2 | 7/2012 | Ota |
| 8,265,793 B2 | 9/2012 | Cross et al. |
| 8,287,522 B2 | 10/2012 | Moses et al. |
| 8,292,807 B2 | 10/2012 | Perkins et al. |
| 8,320,534 B2 | 11/2012 | Kim et al. |
| 8,340,654 B2 | 12/2012 | Bratton et al. |
| 8,340,819 B2 | 12/2012 | Mangaser et al. |
| 8,348,675 B2 | 1/2013 | Dohrmann |
| 8,374,171 B2 | 2/2013 | Cho et al. |
| 8,384,755 B2 | 2/2013 | Wang et al. |
| 8,400,491 B1 | 3/2013 | Panpaliya et al. |
| 8,401,275 B2 | 3/2013 | Wang et al. |
| 8,423,284 B2 | 4/2013 | O'Shea |
| 8,451,731 B1 | 5/2013 | Lee et al. |
| 8,463,435 B2 | 6/2013 | Herzog et al. |
| 8,503,340 B1 * | 8/2013 | Xu ................................ 370/310 |
| 8,515,577 B2 | 8/2013 | Wang et al. |
| 8,527,094 B2 | 9/2013 | Kumar et al. |
| 8,532,860 B2 | 9/2013 | Daly |
| 8,610,786 B2 | 12/2013 | Ortiz |
| 8,612,051 B2 | 12/2013 | Norman et al. |
| 8,639,797 B1 | 1/2014 | Pan et al. |
| 8,670,017 B2 | 3/2014 | Stuart et al. |
| 8,726,454 B2 | 5/2014 | Gilbert et al. |
| 8,780,165 B2 | 7/2014 | Wang et al. |
| 8,836,751 B2 | 9/2014 | Ballantyne et al. |
| 8,849,679 B2 | 9/2014 | Wang et al. |
| 8,849,680 B2 | 9/2014 | Wright et al. |
| 8,861,750 B2 | 10/2014 | Roe et al. |
| 8,897,920 B2 | 11/2014 | Wang et al. |
| 8,902,278 B2 | 12/2014 | Pinter et al. |
| 2001/0002448 A1 | 5/2001 | Wilson et al. |
| 2001/0010053 A1 | 7/2001 | Ben-Shachar et al. |
| 2001/0020200 A1 | 9/2001 | Das et al. |
| 2001/0034475 A1 | 10/2001 | Flach et al. |
| 2001/0034544 A1 | 10/2001 | Mo |
| 2001/0037163 A1 | 11/2001 | Allard |
| 2001/0048464 A1 | 12/2001 | Barnett |
| 2001/0051881 A1 | 12/2001 | Filler |
| 2001/0054071 A1 | 12/2001 | Loeb |
| 2001/0055373 A1 * | 12/2001 | Yamashita ................. 379/90.01 |
| 2002/0015296 A1 | 2/2002 | Howell et al. |
| 2002/0027597 A1 | 3/2002 | Sachau |
| 2002/0027652 A1 | 3/2002 | Paromtchik et al. |
| 2002/0033880 A1 | 3/2002 | Sul et al. |
| 2002/0038168 A1 | 3/2002 | Kasuga et al. |
| 2002/0044201 A1 | 4/2002 | Alexander et al. |
| 2002/0049517 A1 | 4/2002 | Ruffner |
| 2002/0055917 A1 | 5/2002 | Muraca |
| 2002/0057279 A1 | 5/2002 | Jouppi |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0085030 A1 | 7/2002 | Ghani |
| 2002/0095238 A1 | 7/2002 | Ahlin et al. |
| 2002/0095239 A1 | 7/2002 | Wallach et al. |
| 2002/0098879 A1 | 7/2002 | Rheey |
| 2002/0104094 A1 | 8/2002 | Alexander et al. |
| 2002/0106998 A1 | 8/2002 | Presley et al. |
| 2002/0109770 A1 | 8/2002 | Terada |
| 2002/0109775 A1 | 8/2002 | White et al. |

(56) References Cited

U.S. PATENT DOCUMENTS

| | | |
|---|---|---|
| 2002/0111988 A1 | 8/2002 | Sato |
| 2002/0120362 A1 | 8/2002 | Lathan et al. |
| 2002/0128985 A1 | 9/2002 | Greenwald |
| 2002/0130950 A1 | 9/2002 | James et al. |
| 2002/0133062 A1 | 9/2002 | Arling et al. |
| 2002/0141595 A1 | 10/2002 | Jouppi |
| 2002/0143923 A1 | 10/2002 | Alexander |
| 2002/0177925 A1 | 11/2002 | Onishi et al. |
| 2002/0183894 A1 | 12/2002 | Wang et al. |
| 2002/0184674 A1 | 12/2002 | Xi et al. |
| 2002/0186243 A1 | 12/2002 | Ellis et al. |
| 2003/0021107 A1 | 1/2003 | Howell et al. |
| 2003/0030397 A1 | 2/2003 | Simmons |
| 2003/0048481 A1 | 3/2003 | Kobayashi et al. |
| 2003/0050733 A1 | 3/2003 | Wang et al. |
| 2003/0050734 A1 | 3/2003 | Lapham |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0080901 A1 | 5/2003 | Piotrowski |
| 2003/0100892 A1 | 5/2003 | Morley et al. |
| 2003/0104806 A1 | 6/2003 | Ruef et al. |
| 2003/0112823 A1 | 6/2003 | Collins et al. |
| 2003/0114962 A1 | 6/2003 | Niemeyer |
| 2003/0120714 A1 | 6/2003 | Wolff et al. |
| 2003/0126361 A1 | 7/2003 | Slater et al. |
| 2003/0135097 A1 | 7/2003 | Wiederhold et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1 | 8/2003 | Kawakita |
| 2003/0171710 A1 | 9/2003 | Bassuk et al. |
| 2003/0174285 A1 | 9/2003 | Trumbull |
| 2003/0180697 A1 | 9/2003 | Kim et al. |
| 2003/0195662 A1 | 10/2003 | Wang et al. |
| 2003/0199000 A1 | 10/2003 | Valkirs et al. |
| 2003/0206242 A1 | 11/2003 | Choi et al. |
| 2003/0212472 A1 | 11/2003 | McKee |
| 2003/0216833 A1 | 11/2003 | Mukai et al. |
| 2003/0216834 A1 | 11/2003 | Allard |
| 2003/0220541 A1 | 11/2003 | Salisbury et al. |
| 2003/0220715 A1 | 11/2003 | Kneifel et al. |
| 2003/0231244 A1 | 12/2003 | Bonilla et al. |
| 2003/0232649 A1 | 12/2003 | Gizis |
| 2003/0236590 A1 | 12/2003 | Park et al. |
| 2004/0001197 A1 | 1/2004 | Ko et al. |
| 2004/0001676 A1 | 1/2004 | Colgan et al. |
| 2004/0008138 A1 | 1/2004 | Hockley, Jr. et al. |
| 2004/0010344 A1 | 1/2004 | Hiratsuka |
| 2004/0012362 A1 | 1/2004 | Tsurumi |
| 2004/0013295 A1 | 1/2004 | Sabe et al. |
| 2004/0017475 A1 | 1/2004 | Akers et al. |
| 2004/0019406 A1 | 1/2004 | Wang et al. |
| 2004/0024490 A1 | 2/2004 | Mclurkin et al. |
| 2004/0041904 A1 | 3/2004 | Lapalme et al. |
| 2004/0048633 A1* | 3/2004 | Sato et al. ............ 455/556.1 |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0205664 A1 | 10/2004 | Prendergast |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0241981 A1 | 12/2004 | Dothan et al. |
| 2004/0260790 A1 | 12/2004 | Balloni et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick et al. |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | McGee et al. |
| 2005/0264649 A1 | 12/2005 | Chang et al. |
| 2005/0267826 A1 | 12/2005 | Levy et al. |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |

(56) References Cited

U.S. PATENT DOCUMENTS

| | | |
|---|---|---|
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1* | 3/2006 | Vapaakoski ............ 396/439 |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek, Jr. et al. |
| 2006/0142983 A1 | 6/2006 | Sorensen et al. |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Adachi et al. |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0057866 A1* | 3/2007 | Lee ............ H04M 1/0218 348/E7.079 |
| 2007/0064092 A1* | 3/2007 | Sandbeg ............ H04N 7/142 348/14.02 |
| 2007/0078566 A1 | 4/2007 | Wang et al. |
| 2007/0093279 A1 | 4/2007 | Janik |
| 2007/0112700 A1 | 5/2007 | Den et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0170886 A1 | 7/2007 | Plishner |
| 2007/0176060 A1 | 8/2007 | White et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'Andrea et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1* | 7/2008 | Jobs ............ G06F 3/0488 345/173 |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0255703 A1 | 10/2008 | Wang et al. |
| 2008/0263451 A1 | 10/2008 | Portele et al. |
| 2008/0263628 A1 | 10/2008 | Norman et al. |
| 2008/0267069 A1 | 10/2008 | Thielman et al. |
| 2008/0269949 A1 | 10/2008 | Norman et al. |
| 2008/0281467 A1 | 11/2008 | Pinter |
| 2008/0306375 A1 | 12/2008 | Sayler et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1* | 7/2009 | Li et al. ............ 600/301 |
| 2009/0177323 A1 | 7/2009 | Ziegler et al. |
| 2009/0177641 A1 | 7/2009 | Raghavan |
| 2009/0185792 A1* | 7/2009 | Braunstein ............ H04N 21/2223 386/326 |
| 2009/0237317 A1* | 9/2009 | Rofougaran ............ 343/772 |
| 2009/0240371 A1 | 9/2009 | Wang et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0228249 A1 | 9/2010 | Mohr et al. |
| 2010/0268383 A1 | 10/2010 | Wang et al. |
| 2010/0278086 A1 | 11/2010 | Pochiraju et al. |

(56) References Cited

U.S. PATENT DOCUMENTS

| | | |
|---|---|---|
| 2010/0286905 A1 | 11/2010 | Goncalves et al. |
| 2010/0301679 A1 | 12/2010 | Murray et al. |
| 2010/0323783 A1* | 12/2010 | Nonaka et al. ............... 463/23 |
| 2011/0022705 A1 | 1/2011 | Yellamraju et al. |
| 2011/0050841 A1* | 3/2011 | Wang et al. ............... 348/14.05 |
| 2011/0071675 A1 | 3/2011 | Wells et al. |
| 2011/0071702 A1 | 3/2011 | Wang et al. |
| 2011/0072114 A1 | 3/2011 | Hoffert et al. |
| 2011/0153198 A1 | 6/2011 | Kokkas et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0193949 A1 | 8/2011 | Nambakam et al. |
| 2011/0195701 A1 | 8/2011 | Cook et al. |
| 2011/0218674 A1 | 9/2011 | Stuart et al. |
| 2011/0245973 A1 | 10/2011 | Wang et al. |
| 2011/0280551 A1 | 11/2011 | Sammon |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1* | 1/2012 | Maeckel et al. ............... 719/318 |
| 2012/0036484 A1 | 2/2012 | Zhang et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0113856 A1 | 5/2012 | Krishnaswamy |
| 2012/0191246 A1 | 7/2012 | Roe et al. |
| 2012/0191464 A1 | 7/2012 | Stuart et al. |
| 2012/0203731 A1 | 8/2012 | Nelson et al. |
| 2012/0291809 A1 | 11/2012 | Kuhe et al. |
| 2013/0250938 A1 | 9/2013 | Anandakumar et al. |
| 2014/0047022 A1 | 2/2014 | Chan et al. |
| 2014/0085543 A1 | 3/2014 | Hartley et al. |
| 2014/0135990 A1 | 5/2014 | Stuart et al. |
| 2014/0139616 A1 | 5/2014 | Pinter et al. |
| 2014/0155755 A1 | 6/2014 | Pinter et al. |
| 2014/0267552 A1 | 9/2014 | Wang et al. |

FOREIGN PATENT DOCUMENTS

| | | |
|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |
| CN | 1106939 A | 1/2008 |
| CN | 101151614 A | 3/2008 |
| CN | 100407729 C | 7/2008 |
| CN | 1390098 A | 3/2009 |
| CN | 1507260 A | 8/2009 |
| CN | 101730894 A | 6/2010 |
| CN | 1866396 A | 10/2010 |
| CN | 101978365 A | 2/2011 |
| CN | 102203759 A | 9/2011 |
| CN | 101106939 B | 11/2011 |
| EP | 0466492 A2 | 1/1992 |
| EP | 92/488673 A2 | 6/1992 |
| EP | 0981905 | 1/2002 |
| EP | 1262142 A2 | 12/2002 |
| EP | 1304872 A1 | 4/2003 |
| EP | 1536660 B2 | 9/2004 |
| EP | 1536660 A2 | 6/2005 |
| EP | 1573406 A2 | 9/2005 |
| EP | 2005/1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1928310 A2 | 6/2008 |
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 | 12/2010 |
| EP | 2300930 | 3/2011 |
| EP | 2011/2342651 A2 | 7/2011 |
| GB | 2431261 A | 4/2007 |
| JP | 07-194609 A | 8/1995 |
| JP | 07-213753 | 8/1995 |
| JP | 07-248823 | 9/1995 |
| JP | 07257422 | 10/1995 |
| JP | 96/8084328 A | 3/1996 |
| JP | 2008084328 | 3/1996 |
| JP | 8320727 A | 12/1996 |
| JP | 09-267276 | 10/1997 |
| JP | 10079097 A | 3/1998 |
| JP | 10288689 A | 10/1998 |
| JP | 11-220706 A | 8/1999 |
| JP | 2000032319 A | 1/2000 |
| JP | 2000049800 A | 2/2000 |
| JP | 2000079587 A | 3/2000 |
| JP | 2000196876 A | 7/2000 |
| JP | 2001/188124 A | 4/2001 |
| JP | 125641 | 5/2001 |
| JP | 2001147718 A | 5/2001 |
| JP | 179663 | 7/2001 |
| JP | 2001198865 A | 7/2001 |
| JP | 2001198868 A | 7/2001 |
| JP | 2001199356 A | 7/2001 |
| JP | 2002000574 A | 1/2002 |
| JP | 2002/235423 A | 2/2002 |
| JP | 2002046088 A | 2/2002 |
| JP | 2002/112970 A | 4/2002 |
| JP | 2002/101333 A | 5/2002 |
| JP | 2002305743 A | 10/2002 |
| JP | 2002-321180 | 11/2002 |
| JP | 2002355779 A | 12/2002 |
| JP | 2004-181229 A | 7/2004 |
| JP | 524824 T | 8/2004 |
| JP | 261941 | 9/2004 |
| JP | 2004-289379 A | 10/2004 |
| JP | 028066 | 2/2005 |
| JP | 2005028066 A | 2/2005 |
| JP | 2005/059170 A | 3/2005 |
| JP | 2005-111083 A | 4/2005 |
| JP | 2006/508806 A | 3/2006 |
| JP | 2006/109094 A | 4/2006 |
| JP | 2006/224294 A | 8/2006 |
| JP | 2006/246438 A | 9/2006 |
| JP | 2007-7040 A | 1/2007 |
| JP | 2007/081646 A | 3/2007 |
| JP | 2007-232208 A | 9/2007 |
| JP | 2007-316966 A | 12/2007 |
| JP | 2009-125133 A | 6/2009 |
| JP | 2010/064154 A | 3/2010 |
| JP | 2010-532109 A | 9/2010 |
| JP | 2010/532109 A | 9/2010 |
| JP | 246954 | 11/2010 |
| KR | 2006/0037979 A | 5/2006 |
| KR | 2009/0012542 A | 2/2009 |
| KR | 0019479 A | 2/2010 |
| KR | 0139037 | 12/2010 |
| WO | 1993006690 A1 | 4/1993 |
| WO | 1997/042761 A1 | 11/1997 |
| WO | 1998051078 A1 | 11/1998 |
| WO | 1999067067 | 12/1999 |
| WO | 2000/025516 A1 | 5/2000 |
| WO | 2000033726 A1 | 6/2000 |
| WO | 2001/031861 A1 | 5/2001 |
| WO | 2003077745 | 9/2003 |
| WO | 2004/008738 A1 | 1/2004 |
| WO | 2004/012018 A2 | 2/2004 |
| WO | 2004075456 A2 | 9/2004 |
| WO | 2006/012797 A1 | 2/2006 |
| WO | 2006/078611 A1 | 4/2006 |
| WO | 2006044847 A2 | 4/2006 |
| WO | 2007/041295 A2 | 4/2007 |
| WO | 2007041295 A1 | 4/2007 |
| WO | 2007/041038 A1 | 6/2007 |
| WO | 2007/041038 A3 | 6/2007 |

(56) References Cited

FOREIGN PATENT DOCUMENTS

| WO | 2008/100272 | A2 | 8/2008 |
|---|---|---|---|
| WO | 2008/100272 | A2 | 10/2008 |
| WO | 2008/100272 | A3 | 10/2008 |
| WO | 2009/117274 | A2 | 9/2009 |
| WO | 2009/128997 | A1 | 10/2009 |
| WO | 2009/145958 | A2 | 12/2009 |
| WO | 2010/006205 | A1 | 1/2010 |
| WO | 2010/006211 | A1 | 1/2010 |
| WO | 033666 | A1 | 3/2010 |
| WO | 2010/047881 | A1 | 4/2010 |
| WO | 2010/062798 | A1 | 6/2010 |
| WO | 2010/065257 | A1 | 6/2010 |
| WO | 120407 | A1 | 10/2010 |
| WO | 2011/028589 | A2 | 3/2011 |
| WO | 2011/028589 | A3 | 4/2011 |
| WO | 2011/097132 | A2 | 8/2011 |
| WO | 097130 | A2 | 8/2011 |
| WO | 109336 | A2 | 9/2011 |
| WO | 2011/097132 | A3 | 12/2011 |
| WO | 2011/149902 | A2 | 12/2011 |

OTHER PUBLICATIONS

Ishihara, et al., "Intelligent Microrobot DDS (Drug Delivery System) Measured and Controlled by Ultrasonics", IEEE/RSJ, vol. 2, Nov. 3-5, 1991, pp. 1145-115.

Ivanova, Natali, "Master's thesis: Internet Based Interface for Control of a Mobile Robot", Depai tr ilent of Numerical Analysis and Computer Science.

Orini, "Health Care Robotics: A Progress Report", IEEE International Conference on Robotics and Automation Apr. 1997, pp. 1271-1276.

Jenkins, et al., "Telehealth Advancing Nursing Practice", Nursing Outlook, vol. 49, No. 2, Mar./Apr. 2001.

Johanson, "Supporting video-mediated communication over the Internet", Chalmers University of Technology,Dept of Computer Engineering, Gothenburg, Sweden, 2003.

Jouppi, Norman et al., "First Steps Towards Mutually-Immersive Mobile Telepresence", CSCW, '02, New Orleans, LA, Nov. 16-20, 2002.

Jouppi, et al., "Mutually-Immersive Audio Telepresence", Audio Engineering Society Convention Paper presented at 113th Convention, Oct. 2002.

Kanehiro, Fumio et al., "Virtual Humanoid Robot Platform to Develop Controllers of Real Humanoid Robots without Porting", IEEE 2001, pp. 3217-3276.

Kaplan, et al., "An Internet Accessible Telepresence", 1997, 7 pgs.

Keller, et al., "Raven Interface Project", Fall 2001 Document available at: http://upclose.lrdc.pitt.edu/people/louw_assets/Raven_Slides.pps.

Khatib, "Robots in Human Environments", Proc. International Conference on Control, Automation, Robotics, and Vision ICRACV2000, Singapore Dec. 2000, pp. 454-457.

Tahboub, Karim A. et al., "Dynamics Analysis and Control of a Holonomic Vehicle With Continuously Variable Transmission", Journal of Dynamic Systems, Measurement and Control ASME, vol. 124, Mar. 2002, pp. 118-126.

Kuzuoka, et al., "Can The GestureCam Be A Surrogate?", Proceedings of the Fourth European Conference on Computer-Supported Cooperative Work, Sep 10-14, pp. 181-196.

Lane, "Automated Aides", Newsday, Oct. 17, 2000 Document available at: http://www.cs.cum.edu/nursebot/web/press/nd4380.htm.

Lee, et al., "A novel method of surgical instruction: International telementoring", Internet, 1998, pp. 1-4.

Lim, Hun-Ok et al., "Control to Realize Human-like Walking of a Biped Humanoid Robot", IEEE, 2000, pp. 3271-3276.

Linebarger, John M. et al., "Concurrency Control Mechanisms for Closely Coupled Collaboration in Multithreaded Virtual Environments", Presence, Special Issue on Advances in Collaborative VEs 2004.

Loeb, et al., "Virtual Visit: Improving Communication for Those Who Need It Most", Stud Health Technol Inform.; 94 pp. 302-308, 2003.

Long, "HelpMate Robotics, Inc. (Formerly Transitions Research Corporation) Robot Navigation Technology", NIST Special Publication, Mar. 1999,950-1 Document available at: http://www.atp.nist.gov/eao/sp950-1/helpmate.htm.

Luna, Nancy, "Robot a new face on geriatric care", OC Register, Aug. 6, 2003.

Mack, "Minimally invasive and robotic surgery", Internet, IEEE 2001, pp. 568-572.

Mair, "Telepresence—The Technology. And Its Economic and Social Implications", IEEE Technology and Society, 1997.

Martin, Anya, "Days Ahead", Assisted Living Today, vol. 9, Nov./Dec. 2002, pp. 19-22.

McCardle, et al., "The challenge of utilizing new technology in design education", Internet, 2000, pp. 122-127.

Meng, et al., "E-Service Robot in Home Healthcare", Proceedings of the 2000 IEEE/RSJ, International Conference on Intelligent Robots and Systems, 2000, pp. 832-837.

Michaud, "Introducing Nursebot", The Boston Globe, Sep. 11, 2001, pp. 1-5 Document available at: http://www.cs.cmu.edu/nursebot/web/press/globe 3 01/index.html.

Montemerlo, "Telepresence: Experiments in Next Generation Internet", CMU Robotics Institute, Oct. 20, 1998 Document available at: http://www.ri.cmu.edu/creative/archives.htm (Video/Transcript).

Murphy, "Introduction to AI Robotics",A Bradford Book, 2000, pp. 487.

Nakajima, et al., "A Multimedia Teleteaching System sing an Electronic Whiteboard for Two Way Communication of Motion Videos and Chalkboards", IEEE 1993, pp. 436-441.

Ogata, etaL, "Development of Emotional Communication Robot: WAMOEBA-2r—Experimental evaluation", IEEE 2000, pp. 175-180.

Ogata, et al., "Emotional Communication Robot: WAMOEBA-2R—Emotion Model and Evaluation Experiments", Internet, 1999, pp. 1-16.

Oh, et al., "Autonomous Battery Recharging for Indoor Mobile Robots", Proceedings of Australian Conference on Robotics and Automation, 2000 Document available at: http://users.rsise.anu.edu.au/rsl/rsl_papers/ACRA2000/Auto_Recharge_Paper. pdf.

Ojha, A. K., "An application of Virtual Reality in Rehabilitation", IEEE, Apr. 10-13, 1994, pp. 4-6.

Paulos, et al., "A World Wide Web Telerobotic Remote Environment Browser", 1995, http://vive.cs.berkeley.edu/capek.

Paulos, , "Designing Personal Tele-embodiment", IEEE International Conference on Robotics and Automation, 1998, http://www.prop.org/papers/icra98.pdf.

Paulos, Eric J., "Personal Tele-Embodiment", UC Berkeley, Fall 2001.

Paulos, "PRoP: Personal Roving Presence", ACM:CHI Proceedings of CHI '1998, Document available at: http://www.prop.org/papers/chi98.pdf.

Paulos, et al., "Ubiquitous Tele-embodiment: Applications and Implications", International Journal of Human Computer Studies, vol. 46, No. 6, Jun. 1997, pp. 861-877.

Paulos, "Video of PRoP 2 at Richmond Field Station", www.prop.org Printout of Home Page of Website and two-page Transcript of the audio portion of said PRoP Video, May 2001.

Pin, et al., "A New Family of Omnidirectional and Holonomic Wheeled Platforms for Mobile Robots", IEEE, vol. 10, No. 4, Aug. 1994.

Zipperer, Lorri, "Robotic dispensing system", 1999, pp. 1-2.

Zamrazil, Kristie, "Telemedicine in Texas: Public Policy Concerns", House Research Organization Focus Report, Texas House of Representatives, May 5, 2000, pp. 76-22 Document available at: http://www.hro.house.state.tx.us/focus/telemed.pdf.

Yong, et al., "Robot task execution with telepresence using virtual reality technology", Internet, 1998, pp. 1-8.

Yamasaki, et al., "Applying Personal Robots and Active Interface to Video Conference Systems", Internet, 1995, pp. 243-248.

(56) References Cited

OTHER PUBLICATIONS

Rovetta, et al., "A New Telerobotic Application: Remote Laparoscopic Surgery Using Satellites and and optical fiber Networks for Data Exchange", International Journal of Robotics Research, Jun. 1, 1996, pp. 267-279.
Roy, et al., "Towards Personal Service Robots for the Elderly", Internet, Mar. 7, 2002, 7 pgs.
Salemi, et al., "MILO: Personal robot platform", Internet, 2005, pp. 1-6.
Sandt, Frederic et al., "Perceptions for a Transport Robot in Public Environments", IROS, 1997.
Schaeffer, "Care-O-bot: A System for Assisting Elderly or Disabled Persons in Home Environments", Proceedings of AAATE-99, 1999 Document available at: http://morpha.de/download/publications/IPA.
Schulz, D. et al., "Web Interfaces for Mobile Robots in Public Places", IEEE Robotics &Automation Magazine, IEEE, Service Center, Piscataway, NJ, US, vol. 7, No. 1, Mar. 1, 2000, pp. 1-9.
"Inventing the Future: 2000 Years of Discovery", Discovery Channel Canada (Video/Transcript) Jan. 2, 2000.
"ITU-T H.323 Packet-based multimedia communications", ITU, Feb. 1998 Document available at: http://www.itu.int/rec/T-REC-H.323-199802-S/en.
Candelas, Herias et al., "Flexible virtual and remote laboratory for teaching Robotics", FORMATEX 2006; Proc. Advance in Control Education Madrid, Spain Jun. 2006 , pp. 21-23.
Goldenberg, et al., "Telemedicine in Otolaryngology", American Journal of Otolaryngology, vol. 23, No. 1, 2002, pp. 35-43.
"Mobile Robotics Research Group", Mobile Robotics Research Group, Internet, Edinburgh, 2000, pp. 1-2.
"National Energy Research Scientific Computing Center, Berkeley Lab's RAGE Telepresence Robot Captures R&D100 Award", Jul. 2, 2002 Document available at: http://www.nersc.gov/news/newsroom/RAGE070202.php.
"Nomad XR4000 Hardware Manual", Nomadic Technologies, Inc., Mar. 1999.
"Spawar Systems Center, "Robart"", San Diego, CA, 1998 http://web.archive.org/webr/http:/*/www.nosc.mil/robots/land/robart/robart.html http://web.archive.org/web/19981202205636/http://www.nosc.mil/robots/land/robart/robart.html.
Al-Kassab, et al., "A Review of Telemedicine", Journal of Telemedicine and Telecare, vol. 5, Supplement 1, 1999.
Ando, et al., "A Multimedia Self-service Terminal with Conferencing Functions", IEEE, Jul. 5-7, 1995, pp. 357-362.
Android Amusement Corp, "What Marketing Secret . . . Renting Robots from Android Amusement Corp!", (Advertisement) 1982.
Applebome, "Planning Domesticated Robots for Tomorrow's Household", New York Times, Mar. 4, 1982, pp. 21 & 23, http://www.theoldrobots.com/images17/dc17.JPG.
Baltus, et al., "Towards Personal Service Robots for the Elderly, Proceedings for the Elderly Workshop on Interactive Robots and Entertainment", Computer Science and Robotics 2000.
Bar-Cohen, et al., "Virtual reality robotic telesurgery simulations using MEMICA haptic system", Internet Mar. 5, 2001, pp. 1-7.
Bartholomew, "An Apothecary's Pharmacy" Document available at: http://classes.bnf.fr/ema/grands/034.htm.
Bauer, John et al., "Remote telesurgical mentoring: feasibility and efficacy", IEEE, 2000, pp. 1-9.
Bauer, Jeffrey C. et al., "Service Robots in Health Care: The Evolution of Mechanical Solutions to Human Resource Problems", Jun. 2003.
Bischoff, "Design Concept and Realization of the Humanoid Service Robot HERMES", Field and Service Robotics, Springer, London, 1998, pp. 485-492.
Blackwell, Gerry, "Video: A Wireless LAN Killer App?", Internet, Apr. 16, 2002, pp. 1-3.
Breslow, Michael J. et al., "Effect of a multiple-site intensive care unit telemedicine program on clinical and economic outcome An alternative paradigm for intensivist staffing", Critical Care Med; vol. 32, No. 1, Jan. 2004, pp. 31-38.
Brooks, Rodne, "Remote Presence", Abstracts from Flesh & Machines, How Robots Will Change Us, Feb. 2002, pp. 131-147.
Celi, et al., "The EICU: It's not just telemedicine", Critical Care Medicine vol. 29, No. 8 (Supplement), Aug. 2001.
Cheetham, Anastasia et al., "Interface Development for a Child's Video Conferencing Robot", 2000, pp. 1-4.
Cleary, et al., "State of the art in surgical robotics: Clinical applications and technology challenges", Internet, Feb. 24, 2002, pp. 1-26.
CNN, "Floating 'droids' to roam space corridors of the future", Internet, Jan. 12, 2000, pp. 1-4.
cnn.com/iechnology, "Paging R.Robot: Machine helps doctors with patients", Internet, Sep. 30, 2003, pp. 1-3.
Crowley, Susan L., "Hello to Our Future", AARP Bulletin, Jan. 2000 Document available at: http://www.cs.cmu.ed/-nursebot/web/press/aarp 99_14/millennium.html.
Dalton,"Techniques for Web Telerobotics", PhD Thesis, University of Western Australia, 2001, pp. 27-62, 149-191 Document available at: http://telerobot.mech.uwa.edu.au/information.html.
Davies, "Robotics in Minimally Invasive Surgery", Internet, Jun. 6, 1995, p. 5/1-5/2.
Digiorgio, James, "Is Your Emergency Department of the Leading Edge?", Internet, 2005, pp. 1-4.
Elhajj, et al., "Supermedia in Internet-based telerobotic operations", Internet, 2001, pp. 1-14.
Elhajj, et al., "Synchronization and Control of Supermedia Transmission Via the Internet", Proceedings of 2001 International Symposium on Intelligent Multimedia Video and Speech Processing, Hong Kong, May 2-4, 2001.
Ellison, et al., "Telerounding and Patient Satisfaction Following Surgery", 2004, pp. 523-530.
Han, et al., "Construction of an Omnidirectional Mobile Robot Platform Based on Active Dual-Wheel Caster Mechanisms and Development of a Control Simulator", Kluwer Acedemic Publishers, vol. 29, Nov. 2000, pp. 257-275.
Fels, "Developing a Video-Mediated Communication System for Hospitalized Children", Telemedicine Journal, vol. 5, vol. 5, No. 2, 1999.
Fetterman, "Videoconferencing over the Internet", Internet, 2001, pp. 1-8.
Fiorini, P. et al., "Health Care Robotics: A Progress Report", IEEE International Conference on Robotics and Automation, 1997.
Ghiasi, et al., "A Generic Web-based Teleoperations Architecture: Details and Experience", SPIE Conference on Telemanipulator and Telepresence Technologies VI, Sep. 1999.
Goldberg, et al., "Collaborative Teleoperation via the Internet", IEEE International Conference on Robotics and Automation, San Francisco, California, Apr. 2000.
Goldberg, "Desktop Teleoperation via the World Wide Web, Proceedings of the IEEE International Conference on Robotics and Automation", 1995, pp. 654-659 Document available at: http://citeseer.ist.psu.edu/cache/papers/cs/5/ftp:zSzzSzusc.eduzSzpubzSziriszSzraiders.pdf/gol.
Goldberg, "More Online Robots, Robots that Manipulate", Internet, Updated Aug. 2001 Document available at: http://ford.ieor.berkeley.edu/ir/robots_a2.html.
Goldman, Lea, "Machine Dreams", Entrepreneurs, Forbes, May 27, 2002.
Gump, Michael D., "Robot Technology Improves VA Pharmacies", Internet, 2001, pp. 1-3.
Handley, et al., "RFC 2327—SDP Session Description Protocol", Apr. 1998, Document available at: http://www.faqs.org/rfcs/rfc2327.html.
Hanebeck, et al., "ROMAN: a mobile Robotic Assistant for Indoor Service Applications", Proceedings of the 1997 IEEE/RSJ International Conference on Intelligent Robots and Systems, 1997.
Harmo, et al., "Moving Eye -Interactive Telepresence Over Internet With a Ball Shaped Mobile Robot", 2000.
Haule, et al., "Control Scheme for Delayed Teleoperation Tasks", Proceedings of the Pacific Rim Conference on Communications, Computer and Signal Processing, May 17, 1995.
Hees, William P., "Communications Design fora Remote Presence Robot", Jan. 14, 2002.

(56) References Cited

OTHER PUBLICATIONS

Holmberg, "Development of a Holonomic Mobile Robot for Mobile Manipulation Tasks", International Conference on Field and Service Robotics, Pittsburgh, PA, Aug. 1999.
Ishiguro, "Integrating a Perceptual Information Infrastructure with Robotic Avatars: A Framework for TeleExistence", Proceeding of IEEE Conference on Intelligent Robots and Systems.
Shimoga, et al., "Touch and force reflection for telepresence surgery", IEEE, 1994, pp. 1049-1050.
Siegwart, "Interacting Mobile Robots on the Web", Proceedings of the 1999 IEEE International Conference on Robotics and Automation, May 1999.
Simmons, "Xavier: An Autonomous Mobile Robot on the Web", IEEE Robotics and Automation Magazine, 1999, pp. 43-48.
Stephenson, Gary, "Dr. Robot Tested at Hopkins", Internet, Aug. 5, 2003, pp. 1-2.
Stoianovici, et al., "Robotic Tools for Minimally Invasive Urologic Surgery", Internet, Dec. 2002, pp. 1-17.
Suplee, "Mastering the Robot", The Washington Post, Sep. 17, 2000, p. A01, Document available at: http://www.cs.cmu.edu-nursebotlweb/press/wash/index.html.
Zorn, Benjamin G., "Ubiquitous Telepresence", Mar. 5, 1996, Document available at: http://www.cs.colorado.edu/-zorn/utlvision/vision.html.
Tendick, et al., "Human-Machine Interfaces for Minimally Invasive Surgery", IEEE, 1997, pp. 2771-2776.
Thrun, et al., "Probabilistic Algorithms and the Interactive Museum Tour-Guide Robot Minerva", Internet, 2000, pp. 1-35.
Tzafestas, et al., "VR-based Teleoperation of a Mobile Robotic Assistant: Progress Report", Internet, Nov. 2000, pp. 1-23.
Urquhart, Kim, "InTouch's robotic Companion 'beams up' healthcare experts", Medical Device Daily, vol. 7, No. 39, Feb. 27, 2003, pp. 1 & 4.
Weiss, et al., "Telework and video-mediated communication: Importance of real-time, interactive communication for workers with disabilities", California State University Northridge, pp. 1-4, Document available at: http://www.csun.edu/cod/conf/1999/proceedings/session0238.html.
West, et al., "Design of Ball Wheel Mechanisms for Omnidirectional Vehicles with Full Mobility and Invariant Kinematics", Journal of Mechanical Design, vol. 119, Jun. 1997, pp. 153-161.
Yamauchi et al., PackBot: A Versatile Platform for Military Robotics, 2004, Internet, pp. 1-10.
Grow, "Office Coworker Robot," Time Magazine, http://www.time.eom/time/specials/packages/article/0,28804,1936165_1936255_1936640,00.html, Nov. 19, 2001, 2 pgs.
"PictureTel Adds New Features And Functionality To Its Award-Winning Live200 Desktop Videoconferencing System", PR Newswire Association, LLC, Gale, Cengage Learning, http://www.thefreelibrary.com/PictureTel+Adds+New+Features+And+Functionality+To+lts+Awar d-Winning . . . -a019512804, Jun. 13, 1997.
Davis, "Meet iRobot, The Smartest Webcam on Wheels," Wired Magazine, 8.09, http://www.wired.eom/wired/archive/8.09/irobot_pr.html, Sep. 2000, 2 pgs.
United States U.S. Appl. No. 60/449,762, filed, Feb. 24, 2003, Wang, et al., 28 pgs.
Itu, "A Far End Camera Control Protocol for Videoconferences Using H.224", Transmission of Non-Telephone Signals, ITU-T, Telecommunication Standardization Sector of ITU, H.281, Nov. 1994, 12 pages.
"Defendant VGo Communications, Inc.'s Invalidity Contentions Pursuant to the Feb. 27, 2012 Civil Minute Order", U.S. District Court for the Central District of California, in Case No. CV11-9185 Pa, May 2, 2012, 143 pages.
"Magne Charge", Smart Power for Electric Vehicles, General Motors Corporation, U.S. Appl. No. 75/189,637, Registration No. 2114006, Filing Date: Oct. 29, 1996, Aug. 26, 1997, 2 pages.
Defendant-Counterclaimant VGo Communications, Inc.'s Supplemental Invalidity Contentions Pursuant to the Feb. 27, 2012 Civil Minute Order, U.S. District Court for the Central District of California, Case No. CV11-9185 PA, May 14, 2012, 228 pages.
Barrett, Rick, "Video Conferencing Business Soars as Companies Cut Travel; Some Travel Cuts are Permanent", available online at <http://www.ivci.com/international_videoconferencing_news_videoconferencing_news_19.html>, May 13, 2002, 2 pages.
Dudenhoeffer et a., "Command and Control Architectures for Autonomous Micro—Robotic Forces", FY00 Project Report, Idaho National Engineering and Environmental Laboratory, Human Systems Engineering and Sciences Department, Idaho Falls, Apr. 2001, 43 pages.
Elhajj et al., "Real-Time Haptic Feedback in Internet-Based Telerobotic Operation", IEEE International Conference on Electro/Information Technology, Jun. 2000, 10 pages.
Evans et al., "HelpMate: The Trackless Robotic Courier", PYXIS, available online at <http://www.pyxis.com/>, 3 pages.
Fong, Terrence, "Collaborative Control: A Robot-Centric Model for Vehicle Teleoperation", The Robotics Institute Carnegie Mellon University, Nov. 2001, 197 pages.
Reply Brief for Defendant-Appellee VGO Communications, Inc., Appeal from the U.S. District Court for the Central District of California, in Case No. 2:11-cv-9185, Judge Percy Anderson, May 28, 2013, 75 pages.
Appeal from the U.S. District Court for the Central District of California in case No. 11-cv-9185, Judge Percy Anderson, Joint Appendix, vol. I of IV, Jun. 24, 2013, pp. A1-A6357.
Appeal from the U.S. District Court for the Central District of California in case No. 11-cv-9185, Judge Percy Anderson, Joint Appendix, vol. II of IV, Jun. 24, 2013, pp. A6849-A10634.
Appeal from the U.S. District Court for the Central District of California in case No. 11-cv-9185, Judge Percy Anderson, Joint Appendix, vol. III of IV, Jun. 24, 2013, pp. A10654-A15517.
Appeal from the U.S. District Court for the Central District of California in case No. 11-cv-9185, Judge Percy Anderson, Joint Appendix, vol. IV of IV, Jun. 24, 2013, pp. A15677-A18127.
Civil Minutes-General: Case No. Cv 11-9185PA (AJWx), *InTouch Tech., Inc.* v. *VGo Commons, Inc.*, U.S. District Court for the Central District of California, Judge Percy Anderson, Sep. 10, 2012, 7 pages.
Zambroski, James, "CMU, Pitt Developing 'Nursebot'", available online at <http://www.cs.cmu.edu/~nursebot/web/press/tribunereview.html>, retrieved on Jun. 26, 2012, Oct. 27, 2000, 3 pages.
Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.
Reply Brief for Plaintiff-Appellant InTouch Technologies, Inc., Appeal from the U.S. District Court for the Central District of California in Case No. 11-cv-9185, Judge Percy Anderson, Jun. 14, 2013, 39 pages.
"Using your Infrared Cell Phone Camera", Available on <http://www.catsdomain.com/xray/about.htm>, retrieved on Jan. 23, 2014, Courtesy of Internet Wayback Machine, Jan. 30, 2010, 4 pages.
Office Action received for Chinese Patent Application No. 200680044698.0, Nov. 4, 2010, 9 pages of Official Copy and 15 pages of English Translation.
Activmedia Robotics, "Pioneer 2/PeopleBot, Operations Manual, Version 9", Oct. 2001, 78 pages.
Adams, Chris, "Simulation of Adaptive Behavior (SAB'02)—From Animals to Animats 7", Mobile Robotics Research Group, The Seventh International Conference, available online at: <http://www.dai.ed.ac.uk/groups/mrg/MRG.html>, retrieved on Jan. 22, 2014, Aug. 4-11, 2002, 1 page.
Apple Inc., "iPhone", iPhone Series XP-002696350, pp. 1-29.
Weaver et al., "Monitoring and Control Using the Internet and Java", vol. 3, Proceedings of the 25th Annual Conference of the IEEE Industrial Electronics Society, 1999, pp. 1152-1158.
Tyrrell et al., "Teleconsultation in Psychology: The Use of Videolinks for Interviewing and Assessing Elderly Patients", British Geriatrics Society, Age and Ageing, vol. 30, No. 3, May 2001, pp. 191-195.
Blaer et al., "TopBot: Automated Network Topology Detection With a Mobile Robot", IEEE, Proceedings of the 2003 International Conference on Robotics and Automation, Taipei, Taiwan, Sep. 14-19, 2003, pp. 1582-1587.

(56) References Cited

OTHER PUBLICATIONS

Bradner, S., "The Internet Standards Process—Revision 3", Network Working Group, Request for Comments 2026, BCP: 9, Obsoletes: 1602, Category: Best Current Practice, Oct. 1996, pp. 1-36.
Christensen et al., "BeeSoft User's Guide and Reference", Robots for the Real World™, Real World Interface, Inc ., Sep. 26, 1997, 203 pages.
Chu et al., "Detection of Target Mobile Signal Strength", Technical Development, Motorola Inc., Jan. 1999, pp. 205-206.
Dario et al., "A Robot Workstation for Diagnosis and Physical Therapy", IEEE Catalog No. 88TH0234-5, Centro "E. Piaggio" University of Pisa, Italy, 1989, pp. 67-72.
Gostai "Gostai Jazz: Robotic Telepresence", available online at <http://www.gostai.com>, 4 pages.
Leifer et al., "VIPRR: A Virtually In Person Rehabilitation Robot", Proceedings of 1997 International Conference on Rehabilitation Robotics, Apr. 14-15, 1997, 4 pages.
Minsky, Marvin, "Telepresence", OMNI Magazine, Jun. 1980, 6 pages.
Osborn et al., "Quality of Life Technology Center", QoLT Research Overview: A National Science Foundation Engineering Research Center, Carnegie Mellon University of Pittsburgh, 2 pages.
Reynolds et al., "Review of Robotic Telemedicine Utilization in Intensive Care Units (ICUs)", 11th Annual ATA Symposium, Tampa, Florida, 2011, 1 page.
Video Middleware Cookbook, "H.350 Directory Services for Multimedia", 4 pages.
Umass Lowell Robotics Lab, "Robotics Lab @ UMASS Lowell", Department of Computer Science, Brochure, 2011, 2 pages.
Tsui, et al., "Exploring Use Cases for Telepresence Robots", 6th ACM/IEEE International Conference on Human-Robot Interaction (HRI),, Mar. 2011, pp. 11-18.
Tipsuwan et al., "Gain Adaptation of Networked Mobile Robot to Compensate QoS Deterioration", vol. 4, 28th Annual Conference of the Industrial Electronics Society, Nov. 5-8, 2002, pp. 3146-3151.
Active Media, Inc., "Saphira Software Manual", Real World, Saphira Version 5.3, 1997, 105 pages.
Gaidioz et al., "Synchronizing Network Probes to Avoid Measurement Intrusiveness with the Network Weather Service", High-Performance Distributed Computing, Proceedings of the Ninth International Symposium, 2000, pp. 147-154.
Garner et al., "The Application of Telepresence in Medicine", BT Technology Journal, vol. 15, No. 4, Oct. 1, 1997, pp. 181-187.
Jacobs et al., "Applying Telemedicine to Outpatient Physical Therapy", AMIA, Annual Symposium Proceedings, 2002, 1 page.
Kurlowicz et al., "The Mini Mental State Examination (MMSE)", The Hartford Institute for Geriatric Nursing, Journal of Psychiatric Research, No. 3, Jan. 1999, 2 pages.
Lemaire, Edward, "Using Communication Technology to Enhance Rehabilitation Services", Terry Fox Mobile Clinic, The Rehabilitation Centre, Ottawa, Canada, Version 2.0, 1998-2001, 104 pages.
Nakazato et al., "Group-Based Interface for Content-Based Image Retrieval", Proceedings of the Working Conference on Advanced Visual Interfaces, 2002, pp. 187-194.
Nakazato et al., "Group-Oriented User Interface for Digital Image Management", Journal of Visual Languages and Computing, vol. 14, No. 4, Aug. 2003, pp. 45-46.
North, Michael, "Telemedicine: Sample Script and Specifications for a Demonstration of Simple Medical Diagnosis and Treatment Using Live Two-Way Video on a Computer Network", Greenstar Corporation, 1998, 5 pages.
Radvision, "Making Sense of Bandwidth the NetSense Way", Network Congestion in Unmanaged Networks Bandwidth Estimation and Adaptation Techniques, Radvision's Netsense Technology, 2010, 7 pages.
Roy et al., "Towards Personal Service Robots for the Elderly", Workshop on Interactive Robots and Entertainment (WIRE 2000), vol. 25, Apr. 30-May 1, 2000, 7 pages.

Telepresence Research, Inc., "Telepresence Mobile Robot System", available online at <http://www.telepresence.com/telepresence-research/TELEROBOT/>, retrieved on Nov. 23, 2010, Feb. 20, 1995, 3 pages.
Theodosiou et al., "MuLVAT: A Video Annotation Tool Based on XML-Dictionaries and Shot Clustering", 19th International Conference, Artificial Neural Networks-ICANN, Sep. 14-17, 2009, pp. 913-922.
Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.
Roach, Adam, "Automatic Call Back Service in SIP", Internet Engineering Task Force, Internet Draft, Category Informational, Mar. 2000, 8 pages.
Picturetel Corporation, "Introducing PictureTel Live200 for Windows NT", 1997, 63 pages.
Piquepaille, Roland, "How New Technologies are Modifying Our Way of Life", Roland Piquepaille's Technology Trends, This Blog and its RSS Feed Are Moving, Oct. 31, 2004, 2 pages.
Microsofi Corporation, Inc., "Microsoft NetMeeting 3 Features", available online at <http://technet.rnicrosoft.com/en-us/library/cc723477.aspx>, retrieved on Jun. 26, 2012, 2012, 6 pages.
Metz, Cade, "HP Labs", available online at <http://www.pcmag.eom/article2/0,2817,1130820,00.asp>, Jul. 1, 2003, 4 pages.
ITU, "Call Completion Supplementary Services for H.323", ITU-T, Telecommunication Standardization Sector of ITU, H.450.9, Series H: Audiovisual and Multimedia Systems, Nov. 2000, 63 pages.
ITU, "Call Intrusion Supplementary Service for H.323", ITU-T, Telecommunication Standardization Sector of ITU, H.450.11, Series H: Audiovisual and Multimedia Systems, Mar. 2001, 59 pages.
Screenshot Showing Google Date for Lemaire Telehealth Manual, Screenshot Retrieved on Dec. 18, 2014, 1 page.
Appeal from the U.S. District Court for the Central District of California in No. 11-CV-9185, Judge Percy Anderson, May 9, 2014, pp. 1-48.
Google translation of: Innovations Report, From Research Project to Television Star: Care-O-Bot in ZDF series, http://www.innovations-report.de/specials/printa.php?id=5157, Sep. 28, 2001, 2 pages.
MPEG File Format Summary, downloaded from: http://www.fileformat.info/format/mpeg/egff.htm, Feb. 1, 2001, 8 pages.
Nomadic Technologies, Inc., "Nomad Scout Language Reference Manual", Software Version: 2.7, Part No. DOC00002, Jul. 12, 1999, 47 pages.
Nomad Scout User's Manual, Nomadic Technologies, Software Version 2. 7, Part No. DOC00004, Jul. 12, 1999, pp. 1-59.
ACM Digital Library Record, "Autonomous Robots", vol. 11, No. 1, downloaded from http://dl.acm.org/citation.cfm?id=591550andpicked=proxandcfid=360891374andcftoken=35225929, Jul. 2001, 2 pages.
Brenner, Pablo, "A Technical Tutorial on the IEEE 802.11 Protocol", BreezeCOM Wireless Communications, 1997, pp. 1-24.
CMU Course, "16x62 Robot User's Manual", (Describing the Nomad Scout), Carnegie Mellon University, Feb. 1, 2001, 11 pages.
Koenen, Rob, "MPEG-4: a Powerful Standard for Use in Web and Television Environments", KPN Research, downloaded from http://www.w3.org/Architecture/1998/06/Workshop/paper26, Jul. 1, 1998, 4 pages.
Library of Congress, "008—Fixed-Length Data Elements (Nr)", MARC 21 Format for Classification Data, downloaded from http://www.loc.gov/marc/classification/cd008.html, Jan. 2000, pp. 1-14.
Panusopone et al., "Performance Comparison of MPEG-4 and H.263+ for Streaming Video Applications", Circuits Systems Signal Processing, vol. 20, No. 3, 2001, pp. 293-309.
Paulos et al., "Personal Tele-Embodiment", Chapter 9 in Goldberg, et al., ed. "Beyond Webcams", MIT Press, Jan. 4, 2002, pp. 155-167.
Paulos, Eric John, "Personal Tele-Embodiment", OskiCat Catalog Record, UCB Library Catalog, 2001, 3 pages.
Paulos, Eric John, "Personal Tele-Embodiment", Introductory and Cover Pages from 2001 Dissertation including Contents Table, together with E-mails Relating thereto from UC Berkeley Libraries,

(56) References Cited

OTHER PUBLICATIONS as Shelved at UC Berkeley Engineering Library (Northern Regional library Facility), May 8, 2002, 25 pages, including 4 pages of e-mails.

Paulos et al., "Social Tele-Embodiment: Understanding Presence", Autonomous Robots, vol. 11, No. 1, Kluwer Academic Publishers, Jul. 2001, pp. 87-95.

Schraft et al., "Care-O-Bot™: The Concept of a System for Assisting Elderly or Disabled Persons in Home Enviornments", IEEE Proceedings of the 24th Annual Conference of the Industrial Electronics Society, IECON '98, Aug. 31-Sep. 4, 1998, pp. 2476-2481.

NetMeeting, http://web.archive.orgjweb/2006041 723 555 5/http://transcriptions .english, Apr. 17, 2006, 2 pages.

Fulbright et al., "SWAMI: An Autonomous Mobile Robot for Inspection of Nuclear Waste of Storage Facilities", Autonomous Robots, 2, 1995, pp. 225-235.

Hameed et al., "A Review of Telemedicine", Journal of Telemedicine and Telecare, vol. 5, Supplement 1, 1999, 1 page.

Brooks, "A Robust Layered Control System for a Mobile Robot," IEEE Journal of Robotics and Automation, 2 (1), Mar. 1986, 10 pgs.

Davis, "Meet iRobot, The Smartest Webcam on Wheels," Wired Magazine, 8.09, http://www.wired.com/wired/archive/8.09/irobot_pr.html, Sep. 2000, 2 pgs.

Dean, et al., "1992 AAAI Robot Exhibition and Competition," AI Magazine, Spring 1993, 10 pgs.

Grow, "Office Coworker Robot," Time Magazine, http://www.time.com/time/specials/packages/article/0,28804,1936165_1936255_1936640,00.html, Nov. 19, 2001, 2 pgs.

Knight, et al., "Active Visual Alignment of a Mobile Stereo Camera Platform", Proceedings of the IEEE, International Conference on Robotics and Automation, San Francisco, Apr. 24-28, 2000, pp. 3202-3208.

"PictureTel Adds New Features And Functionality To Its Award-Winning Live200 Desktop Videoconferencing System", PR Newswire Association, LLC, Gale, Cengage Learning, http://www.thefreelibrary.com/PictureTel+Adds+New+Features+And+Functionality+To+Its+Award-Winning . . . -a019512804, Jun. 13, 1997.

U.S. Appl. No. 10/783,760, filed Feb. 20, 2004, Wang, et al., 48 pgs.
U.S. Appl. No. 60/449,762, filed Feb. 24, 2003, Wang, et al., 28 pgs.

Weiss, et al., "Pebbles: A Personal Technology for Meeting Education, Social and Emotional Needs of Hospitalised Children", Personal and Ubiquitous Computing 5, Springer-Verlag London Ltd., 2001, pp. 157-168.

\* cited by examiner

PORTABLE TELEPRESENCE APPARATUS

CROSS-REFERENCE TO RELATED APPLICATIONS

This application claims priority to Application No. 61/399,637, titled TELE-ROBOTIC SYSTEM WITH A HAND HELD ROBOTIC FACE, filed on Jul. 14, 2010 and is a continuation-in-part of application Ser. No. 12/548,122, titled PORTABLE REMOTE PRESENCE ROBOT, filed on Aug. 26, 2009, the entire contents of each of which are hereby incorporated by reference herein.

TECHNICAL FIELD

The present disclosure relates generally to the field of telepresence systems. More specifically, the present disclosure relates to portable telepresence systems that include an apparatus remotely controlled through a remote station, where the system includes cameras, monitors, microphones, and speakers to allow for two-way audio-visual communication.

BRIEF DESCRIPTION OF THE DRAWINGS

The present embodiments will become more fully apparent from the following description and appended claims, taken in conjunction with the accompanying drawings. Understanding that the accompanying drawings depict only typical embodiments of the invention and are, therefore, not meant to limit the scope of the invention, the embodiments will be described and explained with specificity and detail through use of the accompanying drawings as listed below.

DETAILED DESCRIPTION OF PREFERRED EMBODIMENTS

It will be readily understood that the components of the embodiments as generally described and illustrated in the Figures herein could be arranged and designed in a wide variety of different configurations. Thus the following more detailed description of various embodiments, as represented in the Figures, is not intended to limit the scope of the invention as claimed, but is merely representative of various embodiments of the invention. In addition, in some cases, well-known structures, materials, or operations are not shown or described in detail in order to avoid obscuring aspects of the invention. Furthermore, the described features, structures, or characteristics may be combined in any suitable manner in one or more embodiments.

The word "exemplary" and the term "for example" are used herein to mean "serving as an example, for instance, or illustration." Any embodiment described herein as "exemplary" or "for example" is not necessarily to be construed as preferred or advantageous over other embodiments. Although various aspects of the embodiments are presented in drawings, the drawings are not necessarily drawn to scale unless specifically indicated.

Disclosed is a telepresence system that includes a portable telepresence apparatus coupled to a remote station. The telepresence apparatus includes a monitor, a camera, a speaker and a microphone. The remote station includes a station monitor, a station camera, a station speaker and a station microphone. The portable telepresence apparatus can be attached to a platform mounted to the ceiling of an ambulance. The portable telepresence apparatus can be used by a physician or healthcare worker at the remote station to provide remote medical consultation. When the patient is moved from the ambulance the portable telepresence apparatus can be detached from the platform and moved with the patient.

Also disclosed is a portable telepresence apparatus with a monitor, a camera, a speaker, a microphone and a viewfinder screen all coupled to a housing. The viewfinder screen allows the user to view the image being captured by camera. The portable telepresence apparatus is a hand held device that can be moved by a holder of the device in response to audio commands from the remote station. The telepresence apparatus can be used by medical personnel to remotely view a patient in a fast and efficient manner.

Figure 1:
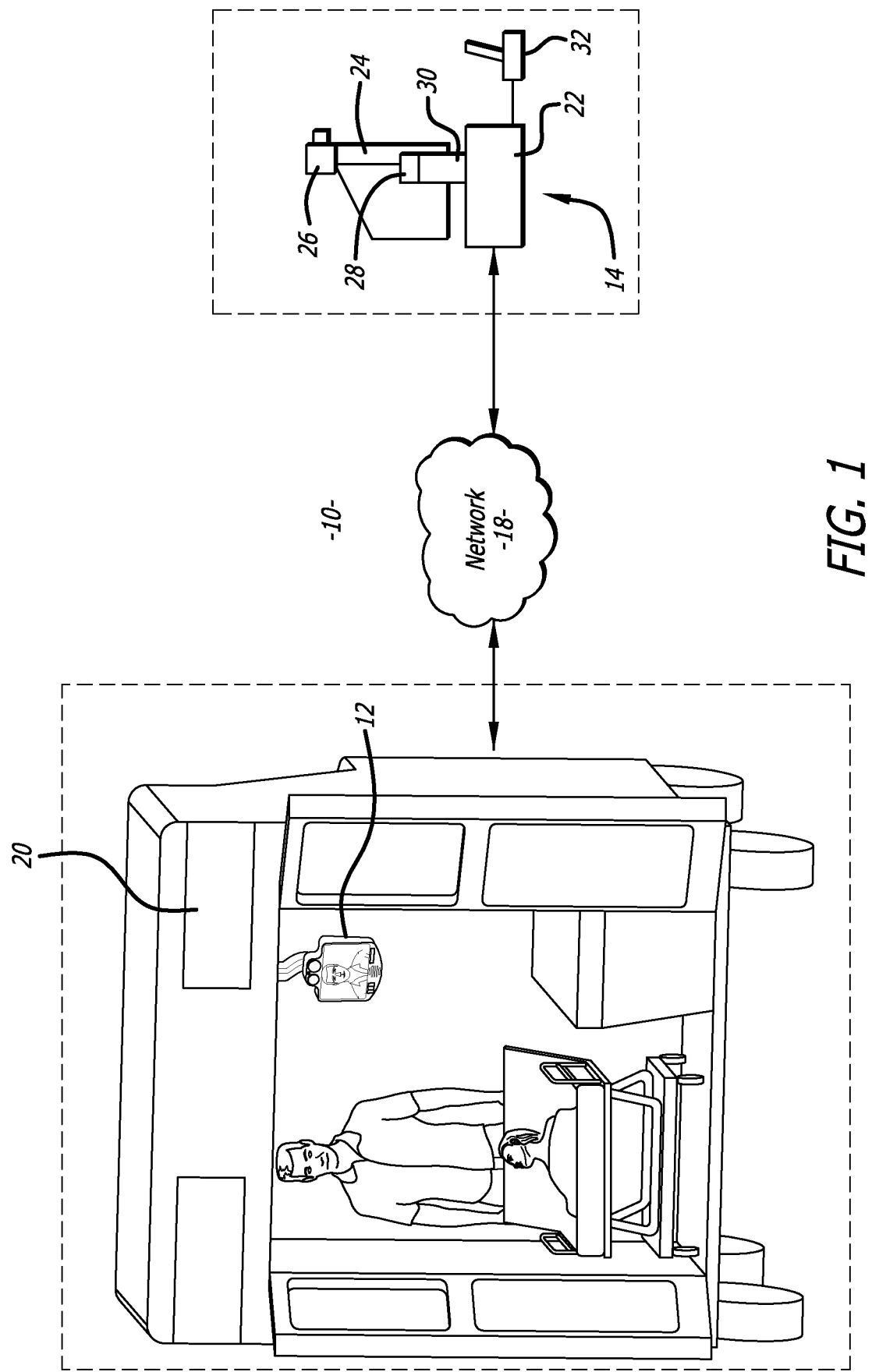
FIG. 1 is an illustration of a telepresence system that includes a remote station coupled to a portable telepresence apparatus located within an ambulance.

Referring to the drawings more particularly by reference numbers, FIG. 1 shows a telepresence system 10. The system 10 includes a portable telepresence apparatus 12 that is coupled to a remote control station 14 through a wireless network 18. The wireless network may be a cellular broadband network, satellite, WiMAX, and/or a WiFi network. The portable telepresence apparatus 12 may be located within an ambulance 20.

The remote control station 14 may include a computer 22 that has a monitor 24, a camera 26, a microphone 28 and a speaker 30. The computer 22 may also contain an input device 32 such as a joystick or a mouse. The control station 14 is typically located in a place that is remote from the telepresence apparatus 12. Although only one remote control station 14 is shown, the system 10 may include a plurality of remote stations 14. In general any number of telepresence apparatus 12 may be coupled to any number of remote stations 14 or other telepresence apparatus 12. For example, one remote station 14 may be coupled to a plurality of telepresence apparatus 12, or one telepresence apparatus 12 may be coupled to a plurality of remote stations 14, or a plurality of telepresence apparatus 12. The system may include an arbitrator (not shown) that controls access between the telepresence apparatus 12 and the remote stations 14.

Figure 2:
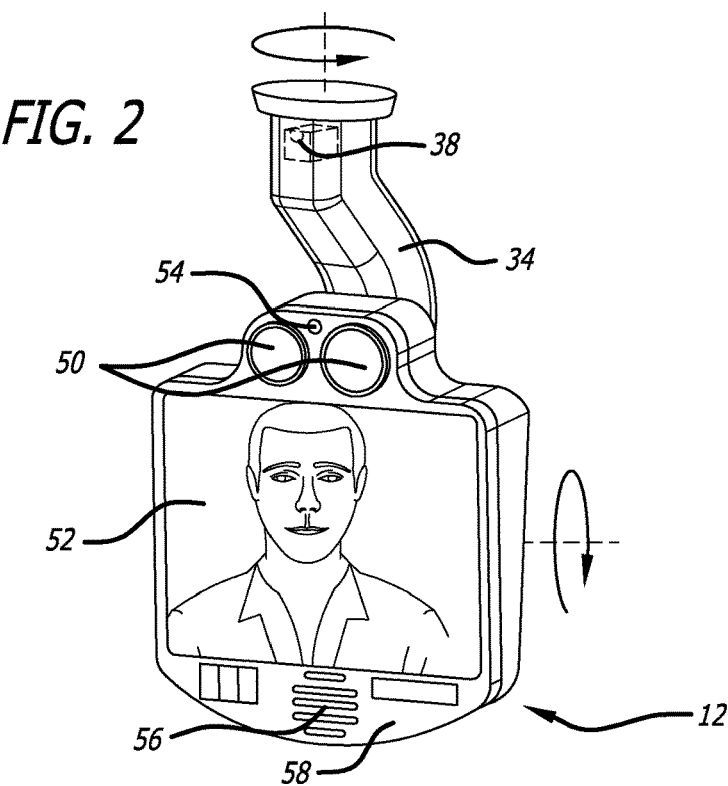
FIG. 2 is an illustration showing the portable telepresence apparatus within the ambulance.
Figure 3:
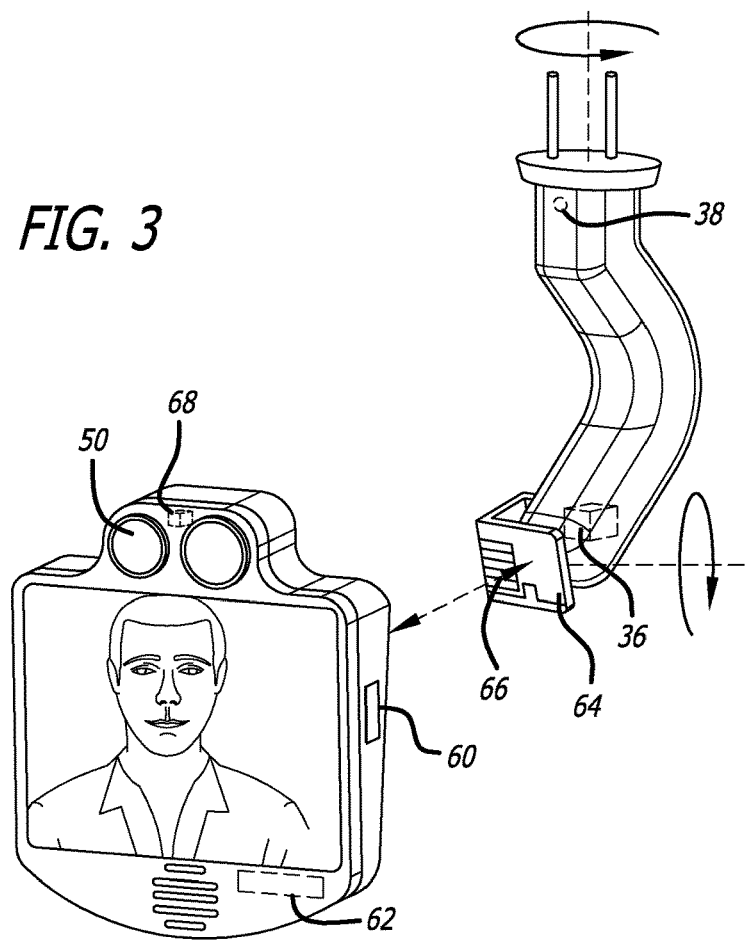
FIG. 3 is an illustration showing the portable telepresence apparatus detached from a platform mounted to the ambulance ceiling.

As shown in FIGS. 2 and 3, the portable telepresence apparatus 12 may be attached to a platform 34. The platform 34 may extend from the ceiling (not shown) of the ambulance 20. The platform 34 may include articulate joints 36 and 38 that provide at least two degrees of freedom and allow a user to move the telepresence apparatus 12 to different positions to view a patient and an EMT within an ambulance.

Each telepresence apparatus 12 includes a camera(s) 50, a monitor 52, a microphone(s) 54 and a speaker(s) 56 that are all attached to a housing 58. The camera 50 is coupled to the remote monitor 24, so that a user at the remote station 14 can view the patient and/or EMT. Likewise, the monitor 52 is coupled to the remote camera 26 so the patient and EMT may view the user of the remote station 14. The microphones 28 and 54, and speakers 30 and 56, allow for audible communication between the system operator and the patient and/or EMT.

The system 10 allows a system user such as a physician to view a patient in the ambulance and provide remote medical consultation through the remote station 14 and the telepresence apparatus 12. Personnel such as the EMT can transmit questions and responses through the system back to the physician. The camera 50 allows the physician to view the patient and enhance the medical consultation. The monitor 52 can display the physician to provide a feeling of presence, such as in an ambulance. The platform 34 allows the physician to pan and tilt the telepresence apparatus 12.

The telepresence apparatus 12 may include a wireless transceiver 60 that is coupled to the wireless network. The portable telepresence apparatus 12 also includes a battery 62.

The system 10 may have certain components and software that are the same or similar to a robotic system provided by InTouch Technologies, Inc. of Goleta, Calif. and embodies a system described in U.S. Pat. No. 6,925,357, which is hereby incorporated by reference.

As shown in FIG. 3, the portable telepresence apparatus 12 can be detached from the platform 34. The telepresence apparatus 12 and platform 34 may have mechanical connectors 64 that allow the telepresence apparatus 12 to be readily attached and detached from the platform 34. Likewise, the telepresence apparatus 12 and platform 34 may include electrical connectors 66. The location where the system 10 is utilized, such as in an ambulance, may include a wireless transceiver (not shown) that can provide wireless communication to the remote control station 14. The electrical connectors 66 provide an electrical connection between the telepresence apparatus 12 and a wireless transceiver. The connectors 66 may also provide power to the telepresence apparatus 12. Alternatively, the wireless transceiver 60 of the telepresence apparatus 12 may be coupled to the remote control station 14 through a wireless transceiver in the vicinity in which the system 10 is utilized, such as in an ambulance. The telepresence apparatus may include an actuator system 68 that can move the camera 50 in two or more degrees of freedom. This allows the operator to move the camera field of view even when the telepresence apparatus 12 is detached from the platform 34.

Figure 4:
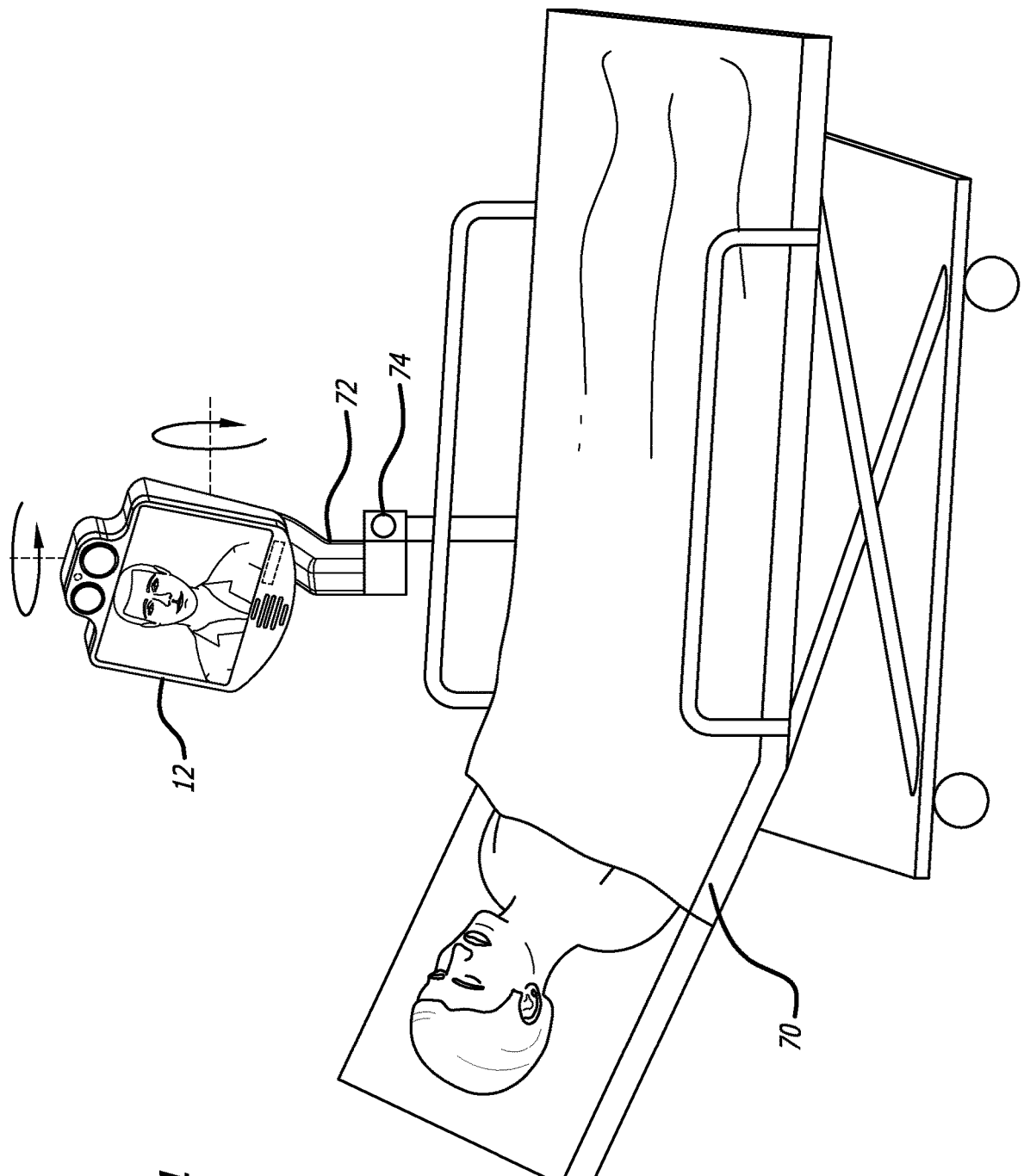
FIG. 4 is an illustration showing the portable telepresence apparatus attached to a patient gurney.

As shown in FIG. 4, the portable telepresence apparatus 12 can be detached from the platform (not shown) and attached to the patient gurney 70. The telepresence apparatus 12 may be attached to a platform 72 with two degrees of freedom that allow the remote station user to move the telepresence apparatus 12. The platform 72 may include a clamp 74 that allows for attachment to the gurney 70. The telepresence apparatus 12 and patient can be moved out of the ambulance on the gurney 70. The portable aspect of the telepresence apparatus 12 allows it to be moved with the patient. The telepresence apparatus 12 should be of a size and weight so that an individual can lift it with ease.

Figure 5:
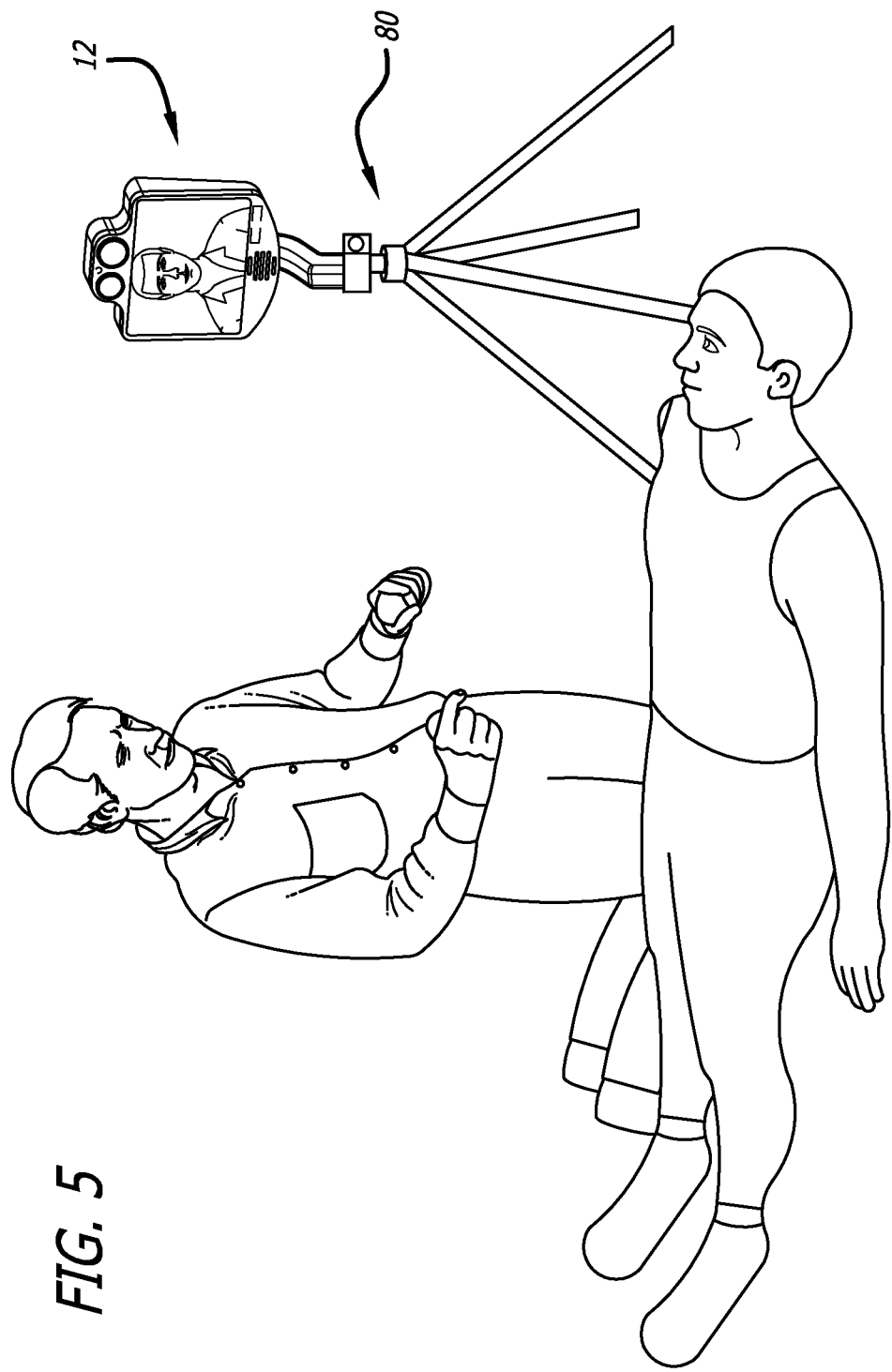
FIG. 5 is an illustration showing the portable telepresence apparatus attached to a stand.

As shown in FIG. 5, the portable telepresence apparatus 12 can be detached from the ambulance platform (not shown) and attached to a stand 80 at a remote location. The portable nature of the telepresence apparatus 12 allows it to be taken to any location to allow for remote telepresence of the operator of the remote station. If the operator is a physician, the portable telepresence apparatus 12 allows for remote medical consultation at any site.

Figure 6:
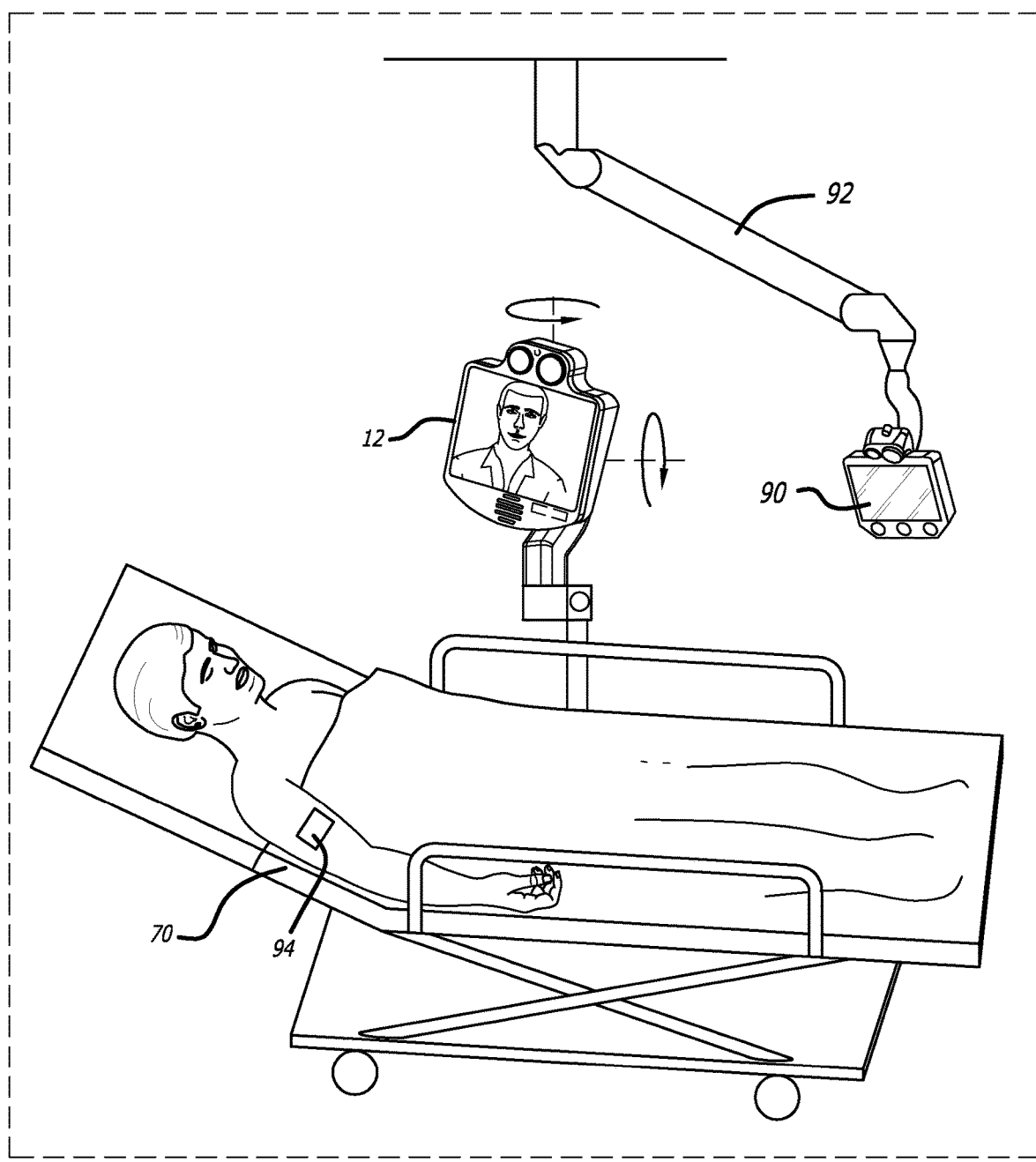
FIG. 6 is an illustration showing a patient within a healthcare facility that has a telepresence apparatus attached to a boom.

FIG. 6 shows the patient and gurney moved into a healthcare facility with a telepresence apparatus 90 attached to a boom 92. When the gurney 70 is moved into close proximity with the healthcare facility, the telepresence apparatus wireless transceiver may be coupled to the remote station through the healthcare facility local wireless network such as a WiFi network. Once inside the facility, the portable telepresence apparatus 90 can be connected to an electrical power outlet and a network for Ethernet connection. An electronic ID device 94 may be attached to the patient. The ID device 94 may transmit a wireless signal to the telepresence apparatus 90 attached to the boom 92. Receipt of the signal by the telepresence apparatus 90 may cause the remote station to be coupled to the telepresence apparatus 90 attached to the boom 92 instead of the portable telepresence apparatus 90. The telepresence apparatus 90 may be coupled to the remote station by other means. For example, a nurse may type in information into the healthcare facility network system that identifies the new location of the patient. Such an entry may cause the system to switch the remote control station to the telepresence apparatus 90. Additionally, there may be other methodologies for inducing the system to automatically transfer the remote station from one telepresence apparatus to another.

Figure 7A:
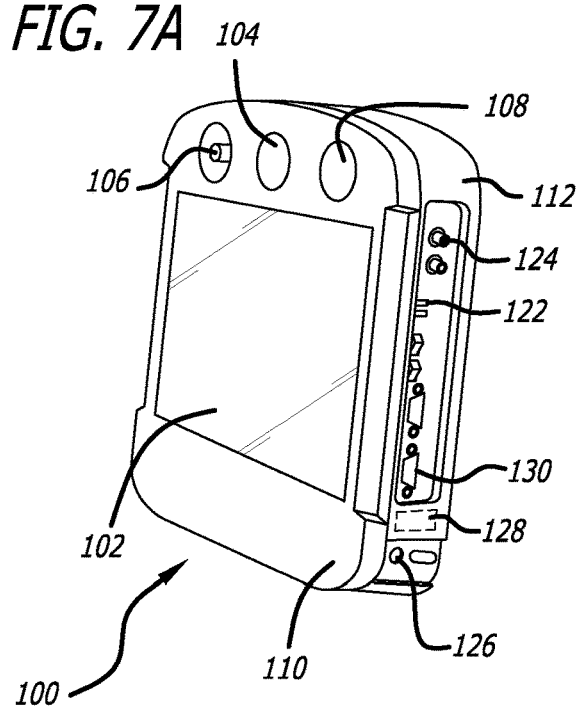
FIGS. 7A and 7B are illustrations of an alternate embodiment of the telepresence apparatus.
Figure 7B:
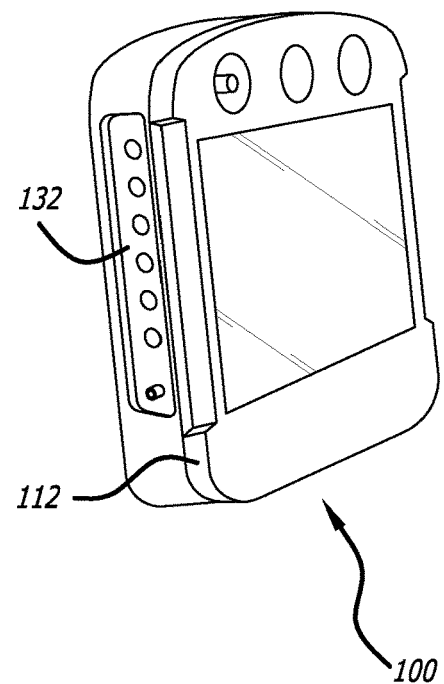
Figure 8:
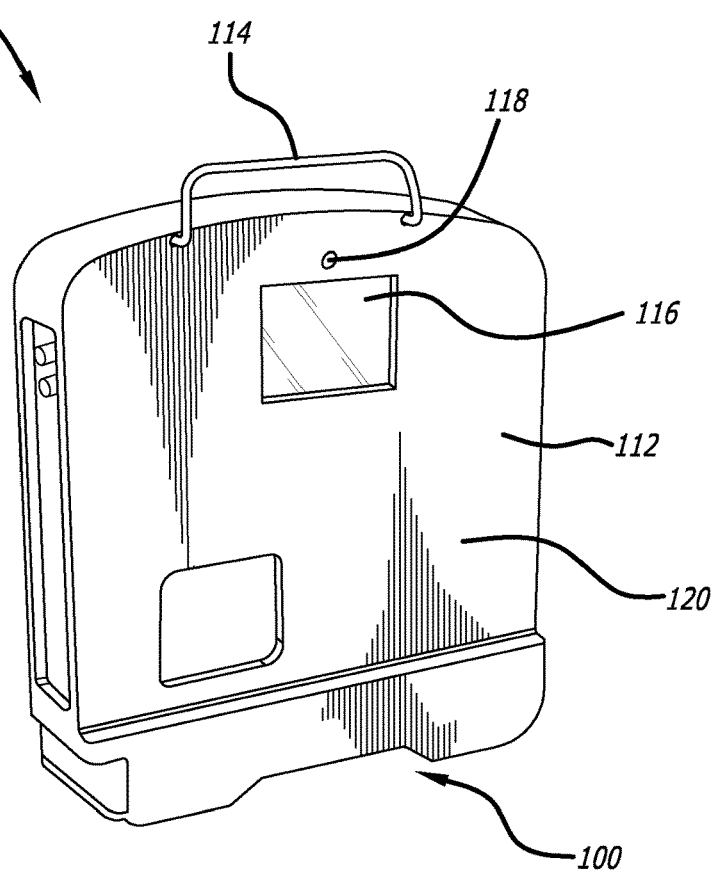
FIG. 8 is an illustration of a rear view of the telepresence apparatus shown in FIG. 7.

FIGS. 7A, 7B and 8 show another embodiment of a portable telepresence apparatus 100. The telepresence apparatus 100 includes a monitor 102, a first camera 104, a microphone 106 and a speaker 108 all attached to a first face 110 of a housing 112. The camera 104 may include a fish eye lens with a 180 degree field of view and a zoom feature. More specifically, the camera is a 10 megapixel CCD. When the remote user is "zoomed out", the system re-samples the 10 MP image to 1440×768 before compressing and sending it over the Internet. The remote user may select a portion of the image, for instance the upper left quarter, by drawing a box around it. The coordinates of this box are transmitted to the telepresence device, which in turn will restrict the re-sampling area to the upper-left 2.5 MP of camera input. The face 100 is constructed to have a size and weight so that it can be carried by a single human being. The telepresence apparatus 100 may have a handle 114 to facilitate carrying and moving it. By way of example, the telepresence apparatus may weigh less than 5 pounds. The housing 112 may be constructed so that the telepresence apparatus 100 can stand in an upright position on a surface, possibly with a lean-back angle of 5 degrees to facilitate viewing.

The telepresence apparatus 100 may include a viewfinder screen 116 and a second camera 118 attached to a second face 120 of the housing 112. The second camera 118 can capture images of a person holding the telepresence apparatus that are transmitted to the remote station, such that the remote user may switch to a view of the holder in order to give them instructions via 2-way audio video communication. Located within the housing 112 are electronic circuits and devices, including a processor(s), memory and hard disk drive (not shown) that can perform the various functions of the telepresence apparatus 100. One side of the telepresence apparatus 100 may include various ports 122, 124, 126, 128 and 130. Port 122 may provide a USB and/or Bluetooth, or other connection. The USB port can be used to attach a medical instrument, such as a stethoscope or a blood pulse oximeter to the telepresence apparatus 100. Port 124 may provide C video, S video auxiliary inputs. A battery of the telepresence apparatus may be charged through connector 126. A cell phone connection may be established through a transceiver 128 within the housing 112. Connector 130 may provide 801.11 WiFi connectivity. As shown in FIG. 7B, the other side of the telepresence apparatus 100 may include different input buttons 132 that can establish videoconferencing controls, such as audio volume adjustment. The monitor 102 may display the various ports and pluggable devices that can be used with the telepresence apparatus 100 through touch screens operated by the user. The system 100 may have certain components and software that are the same or similar to a robotic system provided by InTouch Technologies, Inc. of Goleta, Calif., such as the system described in U.S. Pat. No. 6,925,357, which is hereby incorporated by reference.

Figure 9:
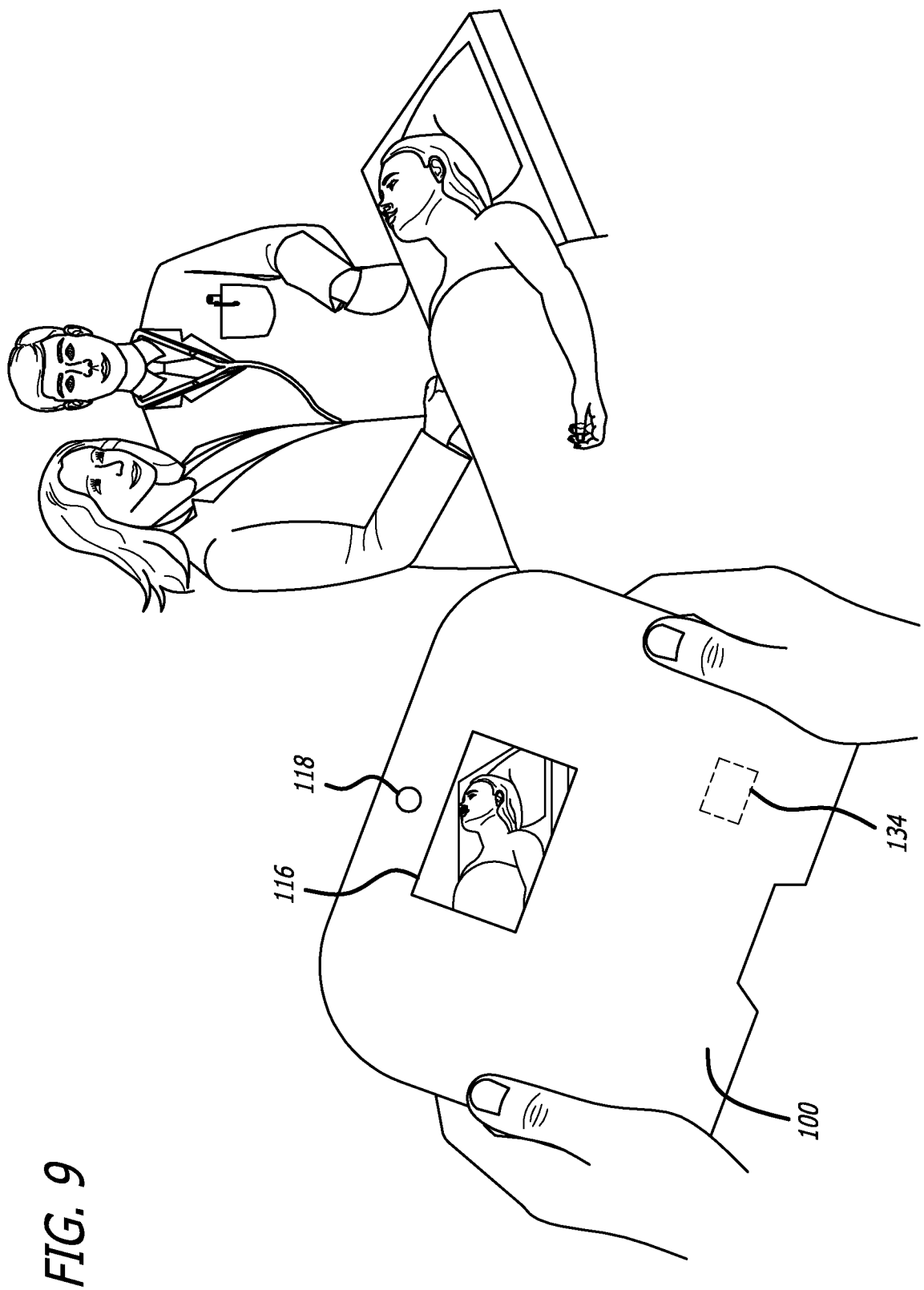
FIG. 9 is an illustration showing a user holding the portable telepresence apparatus while viewing an image captured by the camera through a viewfinder screen.

FIG. 9 shows a user holding the portable telepresence apparatus 100 to allow a remote operator to view a patient through the first camera 104 located on the opposite side of the telepresence apparatus 100. The viewfinder screen 116 allows the holder to view the image being captured by the first camera 104 and move the telepresence apparatus 100, accordingly. By way of example, the operator at the remote station can provide oral instructions to the holder to move the portable telepresence apparatus 100 to obtain a desired view of the patient. To this extent the user performs the functions of the actuators shown in FIGS. 2 and 3, as described above.

The telepresence apparatus 100 may include a motion sensing device 134 such as an accelerometer, gyro and/or magnetometer. The motion sensing device 134 can be utilized, so that the person displayed by the monitor is right sized even if the user is holding the telepresence apparatus 100 in a tilted manner. In other words, the top of the head of the person displayed by the monitor will always be pointing upward and away from gravity, such that if the device is held at a 45 degree angle, the top of the head will appear in the upper-left corner of the screen. Likewise, the motion sensing device 134 can be used to provide a right sized version of an image captured on camera 104 to the remote station.

The viewfinder screen 116 may include touch features that allow the holder of the telepresence apparatus 100 to change the image being captured. For example, movement of the holder's fingers from an inward location in an outward manner may cause the captured image to be zoomed in. An opposite movement of the user's fingers may cause the image to zoom out. Alternatively, the holder may draw on the small touch screen which shows the patient's image, and the resultant telestration may be shared to the remote user. The remote user retains shared feature control, and may disable certain of these features from being available to the holder.

Figure 10:
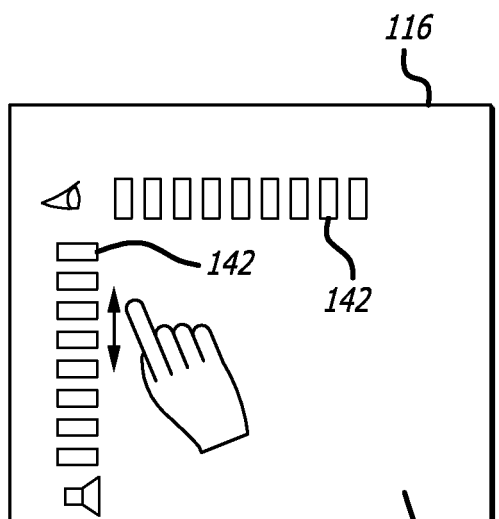
FIG. 10 is an illustration showing a user interface that allows a user to vary speaker and microphone volume.
Figure 11:
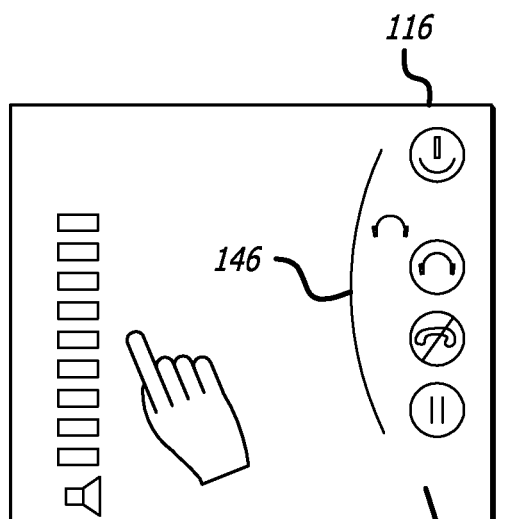
FIG. 11 is an illustration showing a user interface that allows a user to perform certain functions through graphical icons.

FIG. 10 shows a user interface 140 displayed by the viewfinder 116. The interface 140 includes graphical icons 142 that can be touched by the user to change the volume of the speaker and microphone. The viewfinder 116 may also display the interface 144 shown in FIG. 11. The interface 144 includes graphical icons 146 that can be touched to control such functions as power, audio modes, connect/disconnect and a hold button. For example, the user may change the audio source from local microphone to Bluetooth-based headset.

Figure 12:
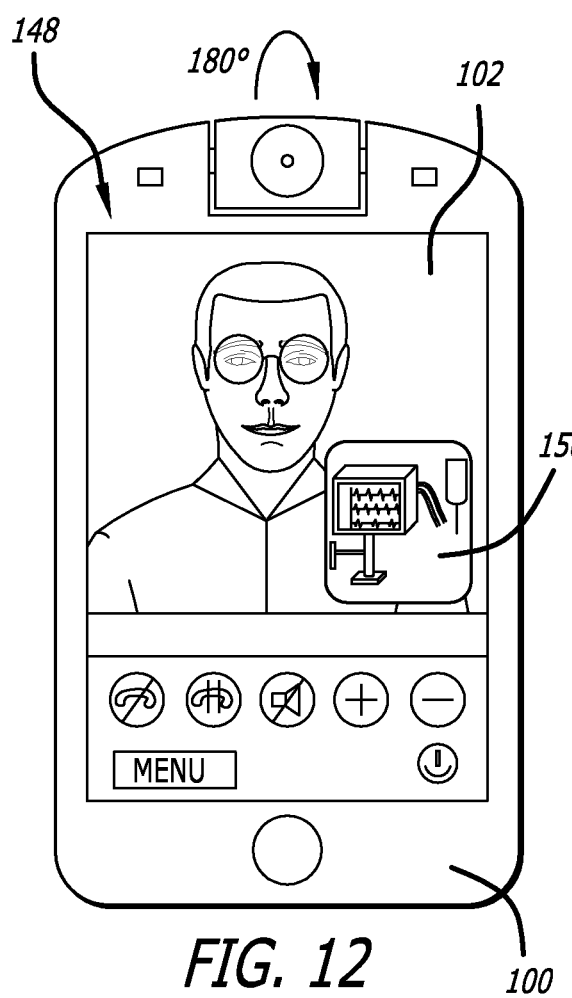
FIG. 12 is an illustration showing a picture in picture display.
Figure 13:
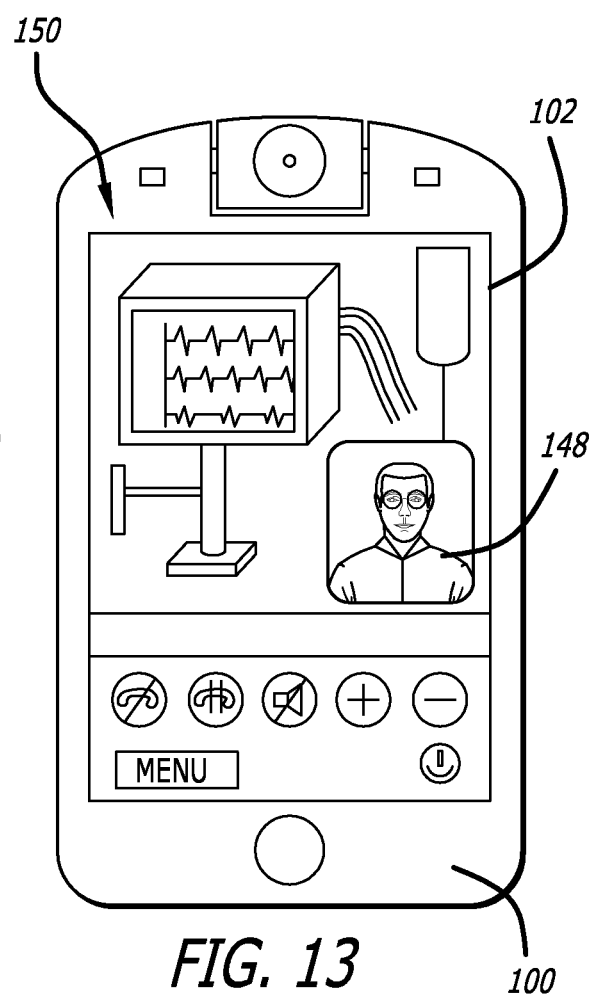
FIG. 13 is an illustration showing the pictures in swapped positions.

FIG. 12 shows the monitor 102 displaying an image 148 of the remote operator and the image 150 captured by the camera in a picture in picture format. The images 148 and 150 can be swapped as shown in FIG. 13. The images can be swapped by a touch screen toggle (not shown) displayed by the viewfinder screen, or by a graphical switch at the remote station. FIGS. 12 and 13 also show an alternative embodiment of the cameras, whereby a single camera can be physically rotated 180 degrees to point either forward or backward.

Figure 14:
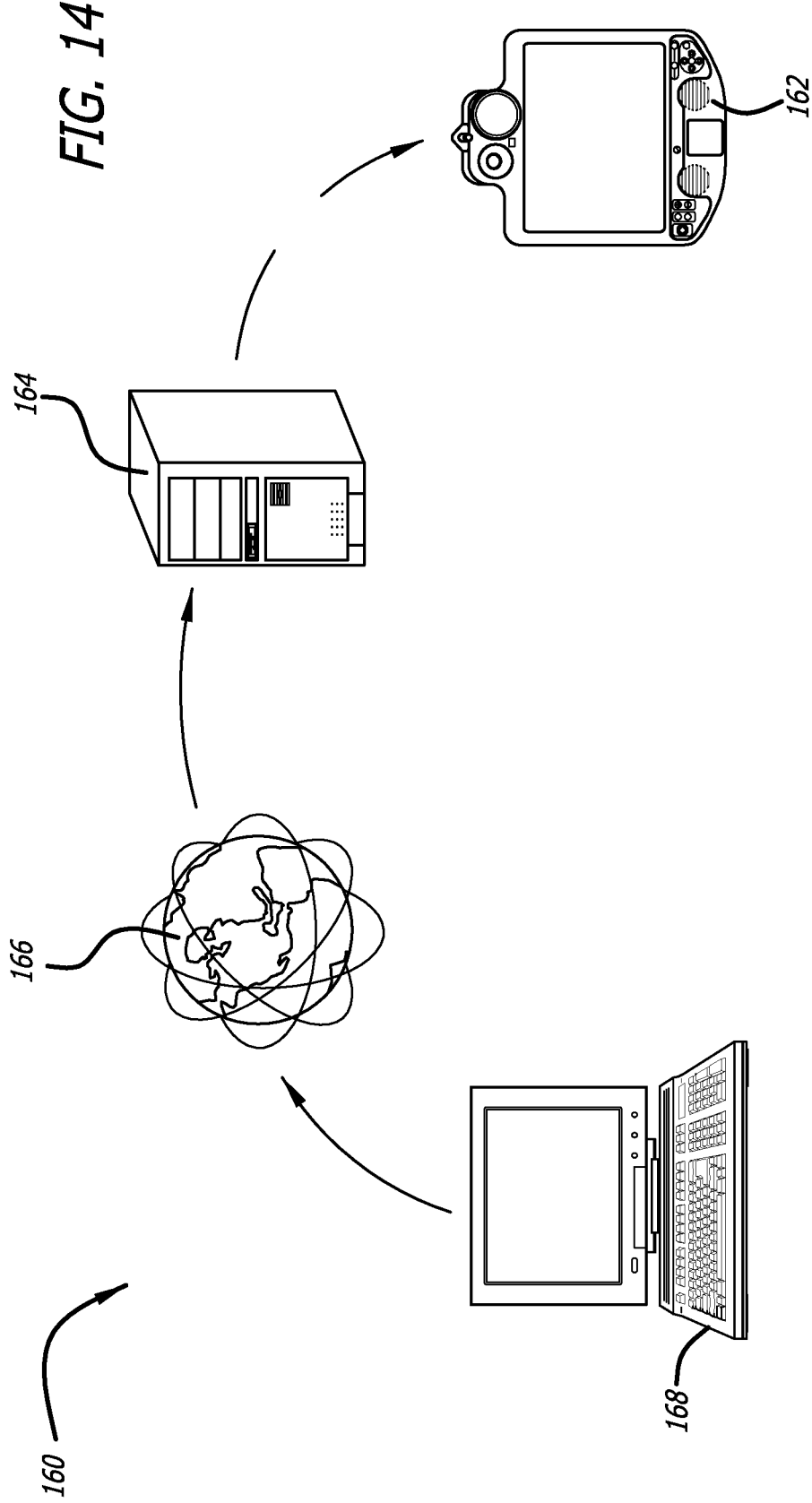
FIG. 14 is an illustration showing a graphical interface showing communication links in the system.

As shown in FIG. 14, the telepresence apparatus and/or the remote station may provide a graphical interface 160 that shows the connectivity between the telepresence apparatus and the remote station. Graphical icons 162, 164, 166 and 168 may represent the telepresence apparatus, a server, the network and remote station, respectively. A solid line between two devices indicates an established link. A broken line indicates a broken communication link between two devices. For example, FIG. 14 depicts a broken communication between the network and remote station. The system can perform diagnostic and corrective action functions for broken links. The corrective actions may be automatic, or include prompt messages to the user to perform certain tasks such as plugging in their Ethernet cable, or provide instructions to configure a firewall. Graphical icon 162 may change depending on the type of telepresence endpoint to which connection is attempted. For example, if the user is attempting a connection to a mobile robot, the icon would depict a mobile robot, whereas if the user is connecting to a head-only device, the icon would depict that device.

The telepresence apparatus 100 may provide simultaneous access to wireless cellular carriers, WiFi and WiMAX local wireless and satellite connectivity using a number of onboard modems. One carrier may operate in accordance with the 2G standard, another on 3G, another on 4G, and so forth. These network connections may exist onboard the telepresence apparatus 100, or alternatively the telepresence apparatus may have a single local wireless connection to a nearby base communications unit, which in turn controls outgoing connectivity. The base communications unit may take the form of a mobile system, which may be mounted in a vehicle, or travel with the telepresence apparatus. The system may also be enhanced with additional amplification stages installed in a vehicle. The system may aggregate available connections and improve Quality of Service metrics in one of a variety of modes. The modes may include: a Redundancy mode that sends the same signal over multiple connections; a Balancing mode that sends parts of a signal over different connections; a Switching mode that sends all traffic over the best available connection; and a VPN switching mode which switches between the Redundancy, Balancing and Switching modes during a session.

The system may evaluate reliability and dynamic bandwidth on each of its wireless connections. Based on current networking statistics, the networking algorithm may choose to split the communication stream among the different connections, for example control commands on one connection and video/audio on another connection, or video on one and control on another connection. When a certain connection degrades significantly, the algorithm may choose to move its data stream to another connection. At times, this may mean giving up video (on a 3G connection) to switch to an audio-only (2G) connection. Further, the algorithm may choose to use a wireless connection which is on an older, slower but more reliable network (e.g. 2G) for audio, and simultaneously use a connection on a newer/faster but less reliable network (e.g. 3G) for video. This approach may ensure that audio is always robustly transported, while the video may have interruptions but will maintain good visual quality and frame rate. Alternatively, the system may have video and audio on the newer/faster connection, with simultaneous backup of audio on the older/slower connection. If the newer connection becomes less reliable, the system may cross-fade the played audio to use the data from the older/slower connection.

The portable telepresence apparatus 100 can be used in various applications. For example, the telepresence apparatus 100 can be used to allow for remote examination of a patient. The telepresence apparatus 100 can remain in an active setup-and-recording mode, even when there is no session with a remote operator in progress. This allows for offline recording of patient status, as well as pre-session "setup". Pre-session setup allows a user to position the telepresence apparatus and use the digital box-zoom controls to ensure optimal viewing of the patient prior to the remote physician's entry. This is to be contrasted with prior art telepresence systems, wherein at the start of a new session, the camera pan/tilt/zoom settings are either at default, or previous settings. The telepresence apparatus allows a local user can set up the optimal view field for the remote doctor prior to his/her session initiation; and further can update the view field when the remote doctor becomes temporarily busy or requests local assistance.

The telepresence apparatus 100 may have an "aircraft mode" that inhibits outbound transmission during take-off and landing when the telepresence apparatus is located in an aircraft, for example. Additionally, the system may be switched to a "capture-then-send" modality during periods of limited wireless connectivity. In this modality, a user can make a video recording of a patient exam intended for a physician. The video recording may be supplemented by telemetry data from attached medical devices. Exam reports are then automatically forwarded to the physician upon the system regaining adequate connectivity, and placed in a queue at the physician's remote station.

The telepresence apparatus may also be equipped with a GPS (not shown). This allows for real-time tracking of the geographic location of each telepresence apparatus, and geo-tagging of session statistics. This serves a variety of functions, including: analysis of wireless connectivity based on geographic location; tracking of video clips and patient data based on proximity to a hospital and ambulance speed; and hospital and billing auditing. The GPS feature may also provide for unique fleet monitoring, anti-theft, etc.

The portable telepresence apparatus can be used for various applications in the medical field. One application is specialty transport, in particular pediatric transport. An ambulance and team can be deployed from Hospital A to Hospital B for patient transport. Upon arrival at Hospital B, a patient may be found to be in need of stabilization prior to transport. An expert consultation can occur in Hospital B, or during transport on the trip back to Hospital A.

For example, a call may be placed for a transport of a patient from a spoke Hospital B which does not have expertise that Hospital A has (e.g., pediatric intensivist specialist care). A transport team from Hospital A is deployed to Hospital B. The team brings the telepresence apparatus 100, mounts it on a gurney and places the gurney in an ambulance. The team arrives at Hospital B and views the patient. If at any point the transport team would like to request a consult, the remote physician from Hospital A establishes a link with the telepresence apparatus located on the gurney. The remote physician can pan-tilt-zoom the image to obtain a desired view. If still unable to access the desired views, someone at the telepresence apparatus side can assist by repositioning the telepresence apparatus 100 and using the viewfinder to help position the front camera on the patient/desired view. The telepresence apparatus side team is able to communicate with the remote physician via the main speaker/mic on the unit. The remote physician may speak with various members of the team and patient/family at Hospital B to make a recommendation. In the event of noisy environment, or privacy situation, a Bluetooth or wireless headset can be used as an alternative. The remote physician is able to help with decisions regarding care/transport of the patient.

Care can be advanced either through decision to continue transport, to not continue transport, or to administer certain care as determined by the remote physician in collaboration with the onsite team. The consult can also occur during transport if there are situations where the patient starts to decompensate. In this case the link would be between a remote station and a telepresence apparatus located in the ambulance during transport of the patient. The telepresence apparatus would be mounted on a gurney, the remote physician can view the patient and communicate with the transport team to help make a care decision.

Another application may include a nurse conducting a scheduled visit to a chronically ill patient in their home. The nurse views the patient. The touch screen of the telepresence apparatus can be used to document various symptoms. The data is stored in the telepresence apparatus. The data and video of certain patient interactions can be forwarded to a server. The telepresence apparatus may receive requested information from the server. The nurse may observe a troubling symptom and request a physician consult. The nurse may call the physician, who establishes a link with the telepresence apparatus and initiates a telehealth session with the patient, facilitated by the nurse. The physician may request that the nurse attach a digital stethoscope to the telepresence apparatus and apply it to the patient. The physician may then request that the nurse attach a portable ultrasound device to the auxiliary video port of the telepresence apparatus. Finally, the physician may decide that the patient should be taken immediately to a medical facility. The nurse may call the ambulance. The nurse stays by the patient's side, with the remote physician logged into the telepresence apparatus, as the patient is transported to the facility.

It will be apparent to those having skill in the art that changes may be made to the details of the above-described embodiments without departing from the underlying principles of the invention. While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. In the claims, the conjunction "and" is inclusive, the conjunction "or" is exclusive and the conjunction "and/or" is either inclusive or exclusive. Embodiments of the invention in which an exclusive property or privilege is claimed are defined as follows.

The invention claimed is:

1. A portable telepresence apparatus coupled to a remote station that has a station monitor, a station camera, a station speaker and a station microphone, the portable telepresence apparatus comprising:
 a hand held housing;
 a first camera coupled to a first face of said housing;
 a monitor that is coupled to said first face of said housing and simultaneously displays a first image captured by the first camera and a station image captured by the station camera;
 a speaker that is coupled to said housing and generates a sound provided through the station microphone;
 a microphone coupled to said housing;
 a battery coupled to said housing;
 a wireless transceiver coupled to said housing; and
 a viewfinder screen coupled to a second face of said housing, wherein the monitor and the viewfinder face different directions and said viewfinder screen displays the first image while said monitor displays the first image and the station image.

2. The portable telepresence apparatus of claim 1, further comprising a second camera coupled to said second face of said housing.

3. The portable telepresence apparatus of claim 1, wherein said viewfinder screen includes at least one touch screen function that can vary the first image.

4. The portable telepresence apparatus of claim 1, further comprising a motion sensing device attached to said housing.

5. The portable telepresence apparatus of claim 4, wherein said motion sensing device is utilized to correct an image displayed by said monitor.

6. The portable telepresence apparatus of claim 4, wherein said motion sensing device is utilized to correct an image provided to the remote station.

7. The portable telepresence apparatus of claim 1, wherein said monitor includes a graphical user interface that allows a user to vary an audio characteristic.

8. The portable telepresence apparatus of claim 1, wherein said housing is configured to be placed on a surface in an upright position.

9. The portable telepresence apparatus of claim 1, wherein said remote station monitor displays hardware icons and depicts a break in a communication link between hardware devices.

10. The portable telepresence apparatus of claim 1, further comprising an actuator system that can move the first camera and is controlled by the remote station.

11. The portable telepresence apparatus of claim 1, further comprising a GPS apparatus.

* * * * *